United States Patent
Hoashi

(10) Patent No.: US 10,252,974 B2
(45) Date of Patent: Apr. 9, 2019

(54) CATIONIC LIPID

(71) Applicant: Takeda Pharmaceutical Company Limited, Osaka (JP)

(72) Inventor: Yasutaka Hoashi, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 15/502,063

(22) PCT Filed: Aug. 6, 2015

(86) PCT No.: PCT/JP2015/072344
§ 371 (c)(1),
(2) Date: Feb. 6, 2017

(87) PCT Pub. No.: WO2016/021683
PCT Pub. Date: Feb. 11, 2016

(65) Prior Publication Data
US 2017/0197903 A1    Jul. 13, 2017

(30) Foreign Application Priority Data
Aug. 7, 2014   (JP) .................................. 2014-161718

(51) Int. Cl.
| | |
|---|---|
| C07C 69/00 | (2006.01) |
| C07C 229/00 | (2006.01) |
| A61K 31/00 | (2006.01) |
| A61K 47/00 | (2006.01) |
| C11C 3/00 | (2006.01) |
| C07C 69/34 | (2006.01) |
| A61K 47/18 | (2017.01) |
| A61K 48/00 | (2006.01) |
| A61K 31/7105 | (2006.01) |
| A61K 31/713 | (2006.01) |
| C07C 229/12 | (2006.01) |
| A61K 9/08 | (2006.01) |
| C12N 15/113 | (2010.01) |
| A61K 9/107 | (2006.01) |
| A61K 9/127 | (2006.01) |

(52) U.S. Cl.
CPC ............... *C07C 69/34* (2013.01); *A61K 9/08* (2013.01); *A61K 31/713* (2013.01); *A61K 31/7105* (2013.01); *A61K 47/18* (2013.01); *A61K 48/00* (2013.01); *C07C 229/12* (2013.01); *C11C 3/003* (2013.01); *A61K 9/107* (2013.01); *A61K 9/127* (2013.01); *C12N 15/113* (2013.01); *C12N 2310/14* (2013.01); *C12N 2320/32* (2013.01)

(58) Field of Classification Search
CPC ... C07C 69/34; C07C 229/12; A61K 31/7105; A61K 31/713; A61K 47/18; C11C 3/003
See application file for complete search history.

(56) References Cited

U.S. PATENT DOCUMENTS

| | | |
|---|---|---|
| 6,043,390 A | 3/2000 | Nantz et al. |
| 2004/0022938 A1 | 2/2004 | Kato et al. |
| 2004/0043952 A1 | 3/2004 | Niedzinski et al. |
| 2013/0108685 A1 | 5/2013 | Kuboyama et al. |
| 2013/0195920 A1 | 8/2013 | Maier et al. |
| 2015/0005363 A1 | 1/2015 | Ansell et al. |

FOREIGN PATENT DOCUMENTS

| | | |
|---|---|---|
| CN | 1455664 | 11/2003 |
| CN | 101780286 | 7/2010 |
| CN | 102884041 | 1/2013 |
| CN | 102898549 | 1/2013 |
| JP | 2002-510713 A | 4/2002 |
| JP | 2009-023972 A | 2/2009 |
| JP | 2015-500835 A | 1/2015 |
| JP | 2015-505838 A | 2/2015 |
| WO | 1999/051729 A1 | 10/1999 |
| WO | 2003/102150 A2 | 12/2003 |

(Continued)

OTHER PUBLICATIONS

The English translation of the International Search Report issued in corresponding International Application No. PCT/JP2015/072344, dated Oct. 16, 2015, 2 pages.

(Continued)

*Primary Examiner* — Sikarl A Witherspoon
(74) *Attorney, Agent, or Firm* — Mintz Levin Cohn Ferris Glovsky and Popeo, P.C.; David G. Conlin; Joohee Lee

(57) ABSTRACT

The present invention provides a technology which enables introduction of an active ingredient (e.g. nucleic acids) into various cells with a high efficiency, and compounds used therefor. The present invention provides a compound represented by the formula:

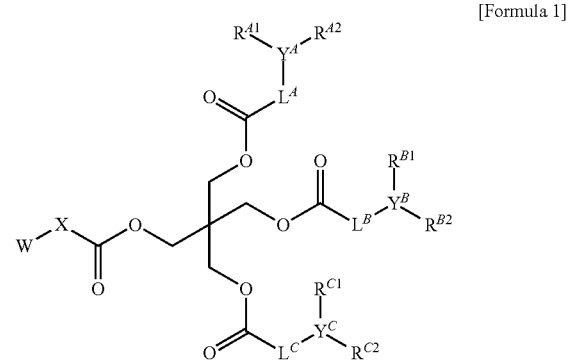

[Formula 1]

[wherein, each symbol is as defined in the present description] or a salt thereof.

8 Claims, No Drawings

Specification includes a Sequence Listing.

(56) References Cited

FOREIGN PATENT DOCUMENTS

| WO | 2010/054401 A1 | 5/2010 |
| WO | 2011/153493 A2 | 12/2011 |
| WO | 2012/054365 A2 | 4/2012 |
| WO | 2013/086322 A1 | 6/2013 |
| WO | 2013/086354 A1 | 6/2013 |
| WO | 2013/126803 A1 | 8/2013 |

OTHER PUBLICATIONS

The Written Opinion of the International Searching Authority issued in corresponding International Application No. PCT/JP2015/072344, dated Oct. 16, 2015, 5 pages.

```
SEQUENCE LISTING

<160> NUMBER OF SEQ ID NOS: 12

<210> SEQ ID NO 1
<211> LENGTH: 21
<212> TYPE: RNA
<213> ORGANISM: Unknown
<220> FEATURE:
<223> OTHER INFORMATION: synthetic construct
<220> FEATURE:
<221> NAME/KEY: modified_base
<222> LOCATION: (4)..(4)
<223> OTHER INFORMATION: 2'-deoxy-2'-fluorouridine
<220> FEATURE:
<221> NAME/KEY: misc_feature
<222> LOCATION: (4)..(5)
<223> OTHER INFORMATION: n is a, c, g, or u
<220> FEATURE:
<221> NAME/KEY: modified_base
<222> LOCATION: (5)..(5)
<223> OTHER INFORMATION: 2'-deoxy-2'-fluorocytidine
<220> FEATURE:
<221> NAME/KEY: modified_base
<222> LOCATION: (7)..(7)
<223> OTHER INFORMATION: 2'-deoxy-2'-fluorouridine
<220> FEATURE:
<221> NAME/KEY: misc_feature
<222> LOCATION: (7)..(10)
<223> OTHER INFORMATION: n is a, c, g, or u
<220> FEATURE:
<221> NAME/KEY: modified_base
<222> LOCATION: (8)..(8)
<223> OTHER INFORMATION: 2'-deoxy-2'-fluorocytidine
<220> FEATURE:
<221> NAME/KEY: modified_base
<222> LOCATION: (9)..(9)
<223> OTHER INFORMATION: 2'-deoxy-2'-fluorouridine
<220> FEATURE:
<221> NAME/KEY: modified_base
<222> LOCATION: (10)..(10)
<223> OTHER INFORMATION: 2'-deoxy-2'-fluorocytidine
<220> FEATURE:
<221> NAME/KEY: modified_base
<222> LOCATION: (14)..(14)
```

```
<223> OTHER INFORMATION: 2'-deoxy-2'-fluorouridine
<220> FEATURE:
<221> NAME/KEY: misc_feature
<222> LOCATION: (14)..(17)
<223> OTHER INFORMATION: n is a, c, g, or u
<220> FEATURE:
<221> NAME/KEY: modified_base
<222> LOCATION: (15)..(15)
<223> OTHER INFORMATION: 2'-deoxy-2'-fluorocytidine
<220> FEATURE:
<221> NAME/KEY: modified_base
<222> LOCATION: (16)..(16)
<223> OTHER INFORMATION: 2'-deoxy-2'-fluorouridine
<220> FEATURE:
<221> NAME/KEY: modified_base
<222> LOCATION: (17)..(17)
<223> OTHER INFORMATION: 2'-deoxy-2'-fluorouridine
<220> FEATURE:
<221> NAME/KEY: modified_base
<222> LOCATION: (19)..(19)
<223> OTHER INFORMATION: 2'-deoxy-2'-fluorocytidine
<220> FEATURE:
<221> NAME/KEY: misc_feature
<222> LOCATION: (19)..(19)
<223> OTHER INFORMATION: n is a, c, g, or u
<220> FEATURE:
<221> NAME/KEY: modified_base
<222> LOCATION: (20)..(20)
<223> OTHER INFORMATION: 2'-deoxythymidine
<220> FEATURE:
<221> NAME/KEY: misc_feature
<222> LOCATION: (20)..(21)
<223> OTHER INFORMATION: phosphorothioate bond
<220> FEATURE:
<221> NAME/KEY: modified_base
<222> LOCATION: (21)..(21)
<223> OTHER INFORMATION: 2'-deoxythymidine

<400> SEQUENCE: 1
ggannannnn aagnnnnann n                                        21

<210> SEQ ID NO 2
<211> LENGTH: 21
<212> TYPE: RNA
<213> ORGANISM: Unknown
<220> FEATURE:
<223> OTHER INFORMATION: synthetic construct
<220> FEATURE:
<221> NAME/KEY: modified_base
<222> LOCATION: (2)..(2)
<223> OTHER INFORMATION: 2'-deoxy-2'-fluorouridine
<220> FEATURE:
<221> NAME/KEY: misc_feature
<222> LOCATION: (2)..(2)
<223> OTHER INFORMATION: n is a, c, g, or u
<220> FEATURE:
<221> NAME/KEY: modified_base
<222> LOCATION: (7)..(7)
<223> OTHER INFORMATION: 2'-deoxy-2'-fluorocytidine
<220> FEATURE:
<221> NAME/KEY: misc_feature
<222> LOCATION: (7)..(9)
<223> OTHER INFORMATION: n is a, c, g, or u
<220> FEATURE:
<221> NAME/KEY: modified_base
<222> LOCATION: (8)..(8)
<223> OTHER INFORMATION: 2'-deoxy-2'-fluorouridine
<220> FEATURE:
<221> NAME/KEY: modified_base
<222> LOCATION: (9)..(9)
<223> OTHER INFORMATION: 2'-deoxy-2'-fluorouridine
<220> FEATURE:
<221> NAME/KEY: modified_base
<222> LOCATION: (14)..(14)
<223> OTHER INFORMATION: 2'-deoxy-2'-fluorouridine
<220> FEATURE:
<221> NAME/KEY: misc_feature
```

```
<222> LOCATION: (14)..(14)
<223> OTHER INFORMATION: n is a, c, g, or u
<220> FEATURE:
<221> NAME/KEY: modified_base
<222> LOCATION: (17)..(17)
<223> OTHER INFORMATION: 2'-deoxy-2'-fluorouridine
<220> FEATURE:
<221> NAME/KEY: misc_feature
<222> LOCATION: (17)..(19)
<223> OTHER INFORMATION: n is a, c, g, or u
<220> FEATURE:
<221> NAME/KEY: modified_base
<222> LOCATION: (18)..(18)
<223> OTHER INFORMATION: 2'-deoxy-2'-fluorocytidine
<220> FEATURE:
<221> NAME/KEY: modified_base
<222> LOCATION: (19)..(19)
<223> OTHER INFORMATION: 2'-deoxy-2'-fluorocytidine
<220> FEATURE:
<221> NAME/KEY: modified_base
<222> LOCATION: (20)..(20)
<223> OTHER INFORMATION: 2'-deoxythymidine
<220> FEATURE:
<221> NAME/KEY: misc_feature
<222> LOCATION: (20)..(21)
<223> OTHER INFORMATION: phosphorothioate bond
<220> FEATURE:
<221> NAME/KEY: modified_base
<222> LOCATION: (21)..(21)
<223> OTHER INFORMATION: 2'-deoxythymidine

<400> SEQUENCE: 2
gnaagannng agangannnn n                                             21

<210> SEQ ID NO 3
<211> LENGTH: 21
<212> TYPE: RNA
<213> ORGANISM: Unknown
<220> FEATURE:
<223> OTHER INFORMATION: synthetic construct
<220> FEATURE:
<221> NAME/KEY: modified_base
<222> LOCATION: (1)..(1)
<223> OTHER INFORMATION: 2'-O-methyl-cytidine
<220> FEATURE:
<221> NAME/KEY: misc_feature
<222> LOCATION: (1)..(3)
<223> OTHER INFORMATION: n is a, c, g, or u
<220> FEATURE:
<221> NAME/KEY: modified_base
<222> LOCATION: (2)..(2)
<223> OTHER INFORMATION: 2'-O-methyl-uridine
<220> FEATURE:
<221> NAME/KEY: modified_base
<222> LOCATION: (3)..(3)
<223> OTHER INFORMATION: 2'-O-methyl-uridine
<220> FEATURE:
<221> NAME/KEY: modified_base
<222> LOCATION: (5)..(5)
<223> OTHER INFORMATION: 2'-O-methyl-cytidine
<220> FEATURE:
<221> NAME/KEY: misc_feature
<222> LOCATION: (5)..(5)
<223> OTHER INFORMATION: n is a, c, g, or u
<220> FEATURE:
<221> NAME/KEY: modified_base
<222> LOCATION: (7)..(7)
<223> OTHER INFORMATION: 2'-O-methyl-cytidine
<220> FEATURE:
<221> NAME/KEY: misc_feature
<222> LOCATION: (7)..(8)
<223> OTHER INFORMATION: n is a, c, g, or u
<220> FEATURE:
<221> NAME/KEY: modified_base
<222> LOCATION: (8)..(8)
<223> OTHER INFORMATION: 2'-O-methyl-uridine
<220> FEATURE:
```

```
<221> NAME/KEY: modified_base
<222> LOCATION: (12)..(12)
<223> OTHER INFORMATION: 2'-O-methyl-uridine
<220> FEATURE:
<221> NAME/KEY: misc_feature
<222> LOCATION: (12)..(12)
<223> OTHER INFORMATION: n is a, c, g, or u
<220> FEATURE:
<221> NAME/KEY: modified_base
<222> LOCATION: (14)..(14)
<223> OTHER INFORMATION: 2'-O-methyl-cytidine
<220> FEATURE:
<221> NAME/KEY: misc_feature
<222> LOCATION: (14)..(17)
<223> OTHER INFORMATION: n is a, c, g, or u
<220> FEATURE:
<221> NAME/KEY: modified_base
<222> LOCATION: (15)..(16)
<223> OTHER INFORMATION: 2'-O-methyl-uridine
<220> FEATURE:
<221> NAME/KEY: modified_base
<222> LOCATION: (17)..(17)
<223> OTHER INFORMATION: 2'-O-methyl-cytidine
<220> FEATURE:
<221> NAME/KEY: modified_base
<222> LOCATION: (20)..(20)
<223> OTHER INFORMATION: 2'-deoxythymidine
<220> FEATURE:
<221> NAME/KEY: misc_feature
<222> LOCATION: (20)..(21)
<223> OTHER INFORMATION: phosphorothioate bond
<220> FEATURE:
<221> NAME/KEY: modified_base
<222> LOCATION: (21)..(21)
<223> OTHER INFORMATION: 2'-deoxythymidine

<400> SEQUENCE: 3
nnnangnnga gnannnngan n                                              21

<210> SEQ ID NO 4
<211> LENGTH: 21
<212> TYPE: RNA
<213> ORGANISM: Unknown
<220> FEATURE:
<223> OTHER INFORMATION: synthetic construct
<220> FEATURE:
<221> NAME/KEY: misc_feature
<222> LOCATION: (20)..(21)
<223> OTHER INFORMATION: phosphorothioate bond
<220> FEATURE:
<221> NAME/KEY: modified_base
<222> LOCATION: (20)..(20)
<223> OTHER INFORMATION: 2'-deoxythymidine
<220> FEATURE:
<221> NAME/KEY: modified_base
<222> LOCATION: (21)..(21)
<223> OTHER INFORMATION: 2'-deoxythymidine

<400> SEQUENCE: 4
ucgaaguacu cagcguaagn n                                              21

<210> SEQ ID NO 5
<211> LENGTH: 21
<212> TYPE: RNA
<213> ORGANISM: Unknown
<220> FEATURE:
<223> OTHER INFORMATION: synthetic construct
<220> FEATURE:
<221> NAME/KEY: modified_base
<222> LOCATION: (1)..(1)
<223> OTHER INFORMATION: 2'-O-methyl-uridine
<220> FEATURE:
<221> NAME/KEY: misc_feature
<222> LOCATION: (1)..(4)
<223> OTHER INFORMATION: n is a, c, g, or u
```

```
<220> FEATURE:
<221> NAME/KEY: modified_base
<222> LOCATION: (2)..(2)
<223> OTHER INFORMATION: 2'-O-methyl-cytidine
<220> FEATURE:
<221> NAME/KEY: modified_base
<222> LOCATION: (3)..(3)
<223> OTHER INFORMATION: 2'-O-methyl-cytidine
<220> FEATURE:
<221> NAME/KEY: modified_base
<222> LOCATION: (4)..(4)
<223> OTHER INFORMATION: 2'-O-methyl-uridine
<220> FEATURE:
<221> NAME/KEY: modified_base
<222> LOCATION: (6)..(6)
<223> OTHER INFORMATION: 2'-O-methyl-uridine
<220> FEATURE:
<221> NAME/KEY: misc_feature
<222> LOCATION: (6)..(6)
<223> OTHER INFORMATION: n is a, c, g, or u
<220> FEATURE:
<221> NAME/KEY: modified_base
<222> LOCATION: (9)..(9)
<223> OTHER INFORMATION: 2'-O-methyl-cytidine
<220> FEATURE:
<221> NAME/KEY: misc_feature
<222> LOCATION: (9)..(10)
<223> OTHER INFORMATION: n is a, c, g, or u
<220> FEATURE:
<221> NAME/KEY: modified_base
<222> LOCATION: (10)..(10)
<223> OTHER INFORMATION: 2'-O-methyl-uridine
<220> FEATURE:
<221> NAME/KEY: modified_base
<222> LOCATION: (12)..(12)
<223> OTHER INFORMATION: 2'-O-methyl-uridine
<220> FEATURE:
<221> NAME/KEY: misc_feature
<222> LOCATION: (12)..(12)
<223> OTHER INFORMATION: n is a, c, g, or u
<220> FEATURE:
<221> NAME/KEY: modified_base
<222> LOCATION: (16)..(16)
<223> OTHER INFORMATION: 2'-O-methyl-uridine
<220> FEATURE:
<221> NAME/KEY: misc_feature
<222> LOCATION: (16)..(19)
<223> OTHER INFORMATION: n is a, c, g, or u
<220> FEATURE:
<221> NAME/KEY: modified_base
<222> LOCATION: (17)..(17)
<223> OTHER INFORMATION: 2'-O-methyl-uridine
<220> FEATURE:
<221> NAME/KEY: modified_base
<222> LOCATION: (18)..(18)
<223> OTHER INFORMATION: 2'-O-methyl-uridine
<220> FEATURE:
<221> NAME/KEY: modified_base
<222> LOCATION: (19)..(19)
<223> OTHER INFORMATION: 2'-O-methyl-uridine
<220> FEATURE:
<221> NAME/KEY: misc_feature
<222> LOCATION: (20)..(21)
<223> OTHER INFORMATION: phosphorothioate bond
<220> FEATURE:
<221> NAME/KEY: modified_base
<222> LOCATION: (20)..(20)
<223> OTHER INFORMATION: 2'-deoxythymidine
<220> FEATURE:
<221> NAME/KEY: modified_base
<222> LOCATION: (21)..(21)
<223> OTHER INFORMATION: 2'-deoxythymidine

<400> SEQUENCE: 5
nnnnangann gnagannnnn n                                        21

<210> SEQ ID NO 6
```

```
<211> LENGTH: 21
<212> TYPE: RNA
<213> ORGANISM: Unknown
<220> FEATURE:
<223> OTHER INFORMATION: synthetic construct
<220> FEATURE:
<221> NAME/KEY: modified_base
<222> LOCATION: (7)..(7)
<223> OTHER INFORMATION: 2'-O-methyl-uridine
<220> FEATURE:
<221> NAME/KEY: misc_feature
<222> LOCATION: (7)..(7)
<223> OTHER INFORMATION: n is a, c, g, or u
<220> FEATURE:
<221> NAME/KEY: modified_base
<222> LOCATION: (9)..(9)
<223> OTHER INFORMATION: 2'-O-methyl-cytidine
<220> FEATURE:
<221> NAME/KEY: misc_feature
<222> LOCATION: (9)..(9)
<223> OTHER INFORMATION: n is a, c, g, or u
<220> FEATURE:
<221> NAME/KEY: modified_base
<222> LOCATION: (13)..(13)
<223> OTHER INFORMATION: 2'-O-methyl-cytidine
<220> FEATURE:
<221> NAME/KEY: misc_feature
<222> LOCATION: (13)..(13)
<223> OTHER INFORMATION: n is a, c, g, or u
<220> FEATURE:
<221> NAME/KEY: modified_base
<222> LOCATION: (15)..(15)
<223> OTHER INFORMATION: 2'-O-methyl-uridine
<220> FEATURE:
<221> NAME/KEY: misc_feature
<222> LOCATION: (15)..(15)
<223> OTHER INFORMATION: n is a, c, g, or u
<220> FEATURE:
<221> NAME/KEY: misc_feature
<222> LOCATION: (20)..(21)
<223> OTHER INFORMATION: phosphorothioate bond
<220> FEATURE:
<221> NAME/KEY: modified_base
<222> LOCATION: (20)..(20)
<223> OTHER INFORMATION: 2'-deoxythymidine
<220> FEATURE:
<221> NAME/KEY: modified_base
<222> LOCATION: (21)..(21)
<223> OTHER INFORMATION: 2'-deoxythymidine

<400> SEQUENCE: 6
aaaaucnana gunanaggan n                                            21

<210> SEQ ID NO 7
<211> LENGTH: 28
<212> TYPE: DNA
<213> ORGANISM: Unknown
<220> FEATURE:
<223> OTHER INFORMATION: synthetic construct

<400> SEQUENCE: 7
ccatcacatt gtagccctct gtgtgctc                                     28

<210> SEQ ID NO 8
<211> LENGTH: 21
<212> TYPE: DNA
<213> ORGANISM: Unknown
<220> FEATURE:
<223> OTHER INFORMATION: synthetic construct

<400> SEQUENCE: 8
cgtcttgctc gagatgtgat g                                            21
```

```
<210> SEQ ID NO 9
<211> LENGTH: 21
<212> TYPE: DNA
<213> ORGANISM: Unknown
<220> FEATURE:
<223> OTHER INFORMATION: synthetic construct

<400> SEQUENCE: 9
ccagcaggtc agcaaagaat t                                              21

<210> SEQ ID NO 10
<211> LENGTH: 27
<212> TYPE: DNA
<213> ORGANISM: Unknown
<220> FEATURE:
<223> OTHER INFORMATION: synthetic construct

<400> SEQUENCE: 10
atcaagatca ttgctcctcc tgagcgc                                        27

<210> SEQ ID NO 11
<211> LENGTH: 18
<212> TYPE: DNA
<213> ORGANISM: Unknown
<220> FEATURE:
<223> OTHER INFORMATION: synthetic construct

<400> SEQUENCE: 11
cctggcaccc agcacaat                                                  18

<210> SEQ ID NO 12
<211> LENGTH: 20
<212> TYPE: DNA
<213> ORGANISM: Unknown
<220> FEATURE:
<223> OTHER INFORMATION: synthetic construct

<400> SEQUENCE: 12
gccgatccac acggagtact                                                20
```

CATIONIC LIPID

CROSS REFERENCE TO RELATED APPLICATIONS

This application is the U.S. national stage pursuant to 35 U.S.C. § 371, of Japanese International Application Ser. No. PCT/JP2015/072344, filed Aug. 6, 2015 and published in Japanese on Feb. 11, 2016 as publication WO 2016/021683 A1, which claims the benefit of Japanese Patent Application Serial No. 2014-161718, filed Aug. 7, 2014, the entire contents of which are hereby incorporated by reference in their entirety.

REFERENCE TO A "SEQUENCE LISTING," A TABLE, OR A COMPUTER PROGRAM LISTING APPENDIX SUBMITTED AS AN ASCII FILE

The Sequence Listing written in file 048497-665N01US_SL.txt, created Jan. 29, 2019, 9,063 bytes, machine format IBM-PC, MS Windows operating system, is hereby incorporated by reference.

TECHNICAL FIELD

The present invention relates to a cationic lipid which enable introduction of active ingredients, in particular, nucleic acids, into various cells, tissues or organs. The present invention further relates to lipid particles containing said cationic lipid or compositions containing an active ingredient and said cationic lipid.

BACKGROUND OF THE INVENTION

In recent times, research and development on nucleic acid medicines, which contain nucleic acids as an active ingredient, has intensively been conducted. Plenty of researches have been conducted, for example, on nucleic acid medicines comprising nucleic acids such as siRNA, miRNA, miRNA mimic or antisense oligonucleotide, having a resolving action or function-suppressing action against a target mRNA. In addition, researches on nucleic acid medicines for expressing a target protein in cells have been conducted. In connection with these research and development, technologies for introducing nucleic acids with a high efficiency into cells, tissues or organs as drug delivery systems (DDS) technologies have been being developed.

As the above mentioned DDS technologies, a technology introducing nucleic acids into cells after mixing the nucleic acid and lipids to form a complex via said complex has traditionally been known. As lipids used for forming the above mentioned complex, cationic lipids, hydrophilic polymer lipids or helper lipids are traditionally known. As the above mentioned cationic lipids, compounds described in Patent Literature 1 to 5 are known.

PRIOR ART REFERENCES

Patent Literature

[Literature 1] WO03/102150 pamphlet
[Literature 2] WO2011/153493 pamphlet
[Literature 3] WO2013/126803 pamphlet
[Literature 4] WO2012/054365 pamphlet
[Literature 5] WO2010/054401 pamphlet

SUMMARY OF THE INVENTION

Problems to be Solved by the Invention

Cationic lipids which enable introduction of nucleic acids into cells with a high efficiency are expected to contribute for creation of nucleic acid medicines, which are beneficial in exertion of a pharmacological effect and safety (low toxicity). In addition, cationic lipids which enable introduction of nucleic acids into cells are expected to enable creation of nucleic acid medicines for various diseases which occur in various tissues. To date, however, those which sufficiently satisfy these matters are yet to be found out.

The objective of the present invention resides in providing a technology which enables introduction of an active ingredient, in particular, nucleic acids, with a high efficiency into cells, and cationic lipids used therefor. In addition, in a different view point, the objective of the present invention resides in providing a technology which enables introduction of an active ingredient, in particular, nucleic acids, into cells, and compounds used therefor.

Means to Solve the Problem

Having studied with a view to solving the above mentioned problem, the inventors found out that the above problem could be solved by using compounds represented by the following formula or a salt thereof to complete the present invention. Namely, the present invention relates at least to the invention below:

[1] A compound represented by the formula:

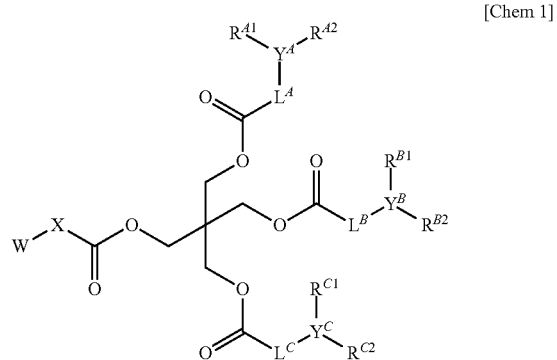

[Chem 1]

[wherein,
W denotes formula —$NR^1R^2$ or formula —$N^+R^3R^4R^5$ ($Z^-$);
$R^1$ and $R^2$ denote, each independently, a $C_{1-4}$ alkyl group or hydrogen atom;
$R^3$, $R^4$ and $R^5$ denote, each independently, a $C_{1-4}$ alkyl group;
$Z^-$ denotes a negative ion;
X denotes a $C_{1-6}$ alkylene group which may be substituted;
$Y^A$, $Y^B$ and $Y^C$ denote, each independently, a methine group which may be substituted;
$L^A$, $L^B$ and $L^C$ denote, each independently, a methylene group which may be substituted or a bond; and
$R^{A1}$, $R^{A2}$, $R^{B1}$, $R^{B2}$, $R^{C1}$ and $R^{C2}$ denote, each independently, a $C_{4-10}$ alkyl group which may be substituted] or a salt thereof (In the present description, abbreviation "compound (I)" or "the present inventive compound" may be used).

[2] The compound according to [1] above or a salt thereof, wherein
$R^1$, $R^2$, $R^3$, $R^4$ and $R^5$ are a methyl group;
$Z^-$ is a halide ion;
X is an ethylene group, trimethylene group or tetramethylene group;
$Y^A$, $Y^B$ and $Y^C$ are a methine group;
$L^A$, $L^B$ and $L^C$ are, each independently, a bond or methylene group; and
$R^{A1}$, $R^{A2}$, $R^{B1}$, $R^{B2}$, $R^{C1}$ and $R^{C2}$ are, each independently, a butyl group, pentyl group or hexyl group.

[3] 3-((5-(dimethylamino)pentanoyl)oxy)-2,2-bis(((2-pentylheptanoyl) oxy)methyl)propyl 2-pentylheptanoate or a salt thereof.

[4] 3-((5-(dimethylamino)pentanoyl)oxy)-2,2-bis(((3-pentyloctanoyl) oxy)methyl)propyl 3-pentyloctanoate or a salt thereof.

[5] A salt of N,N,N-trimethyl-5-oxo-5-(3-((3-pentyloctanoyl)oxy)-2,2-bis(((3-pentyloctanoyl)oxy)methyl) propoxy)pentane-1-aminium and a negative ion.

[6] A lipid particle containing the compound or a salt thereof according to [1]-[5] above.

[7] A composition containing an active ingredient and the compound or a salt thereof according to [1]-[5] above.

[8] The composition according to [7] above, wherein the active ingredient is a nucleic acid.

[9] The composition according to [8] above, wherein the nucleic acid is siRNA or mRNA.

Effect of the Invention

By the present invention, an active ingredient, in particular, nucleic acids, could successfully be introduced into cells, tissues or organs with an excellent efficiency. In addition, by the present invention, an active ingredient (in particular, nucleic acids) could successfully be introduced into various cells, tissues or organs (e.g. a liver, cancer, adipose, bone marrow, hematopoietic cells). By the present invention, a medicine or research agent for introducing an active ingredient (in particular, nucleic acids) into various cells, tissues or organs could successfully be obtainable. Furthermore, by the present invention, if an active ingredient has been introduced into cells, tissues or organs introducing, a high expression efficiency for activity (e.g. pharmacological effect) of the active ingredient is available.

DETAILED DESCRIPTION OF THE INVENTION

Hereinafter, the compound of the present invention, a method for producing the same and use of the same will be described in detail.

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkyl-sulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkenyl group, a cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following substituent group A.

[Substituent Group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,

(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl)($C_{1-6}$ alkyl-carbonyl)amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 hetero atoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 hetero atoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 hetero atoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the aforementioned substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxycarbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkyl-phosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted amino group include an amino group, a mono- or di-(optionally halogenated $C_{1-6}$ alkyl)amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl)amino group (e.g., methylcarbamoylamino), a (mono- or di-$C_{7-16}$ aralkyl-carbamoyl)amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl)($C_{1-6}$ alkyl-carbonyl)amino group (e.g., N-acetyl-N-methylamino) and a ($C_{1-6}$ alkyl)($C_{6-14}$ aryl-carbonyl)amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from substituent group A".

Preferable examples of the optionally substituted silyl group include a tri-$C_{1-6}$ alkylsilyl group (e.g., trimethylsilyl, tert-butyl(dimethyl)silyl).

In the present specification, examples of the "$C_{1-6}$ alkylene group" include —CH$_2$—, —(CH$_2$)$_2$—, —(CH$_2$)$_3$—, —(CH$_2$)$_4$—, —(CH$_2$)$_5$—, —(CH$_2$)$_6$—, —CH(CH$_3$)—, —C(CH$_3$)$_2$—, —CH(C$_2$H$_5$)—, —CH(C$_3$H$_7$)—, —CH(CH(CH$_3$)$_2$)—, —(CH(CH$_3$))$_2$—, —CH$_2$—CH(CH$_3$)—, —CH(CH$_3$)—CH$_2$—, —CH$_2$—CH$_2$—C(CH$_3$)$_2$—, —C(CH$_3$)$_2$—CH$_2$—CH$_2$—, —CH$_2$—CH$_2$—CH$_2$—C(CH$_3$)$_2$— and —C(CH$_3$)$_2$—CH$_2$—CH$_2$—CH$_2$—.

In the present specification, examples of the "$C_{2-6}$ alkenylene group" include —CH=CH—, —CH$_2$—CH=CH—, —CH=CH—CH$_2$—, —C(CH$_3$)$_2$—CH=CH—, —CH=CH—C(CH$_3$)$_2$—, —CH$_2$—CH=CH—CH$_2$—, —CH$_2$—CH$_2$—CH=CH—, —CH=CH—CH₂—CH₂—, —CH=CH—CH=CH—, —CH=CH—CH₂—CH₂—CH₂— and —CH₂—CH₂—CH₂—CH=CH—.

In the present specification, examples of the "$C_{2-6}$ alkynylene group" include —C≡C—, —CH₂—C≡C—, —C≡C—CH₂—, —C(CH₃)₂—C≡C—, —C≡C—C(CH₃)₂—, —CH₂—C≡C—CH₂—, —CH₂—CH₂—C≡C—, —C≡C—CH₂—CH₂—, —C≡C—C≡C—, —C≡C—CH₂—CH₂—CH₂— and —CH₂—CH₂—CH₂—C≡C—.

In the present specification, examples of the "hydrocarbon ring" include a $C_{6-14}$ aromatic hydrocarbon ring, $C_{3-10}$ cycloalkane and $C_{3-10}$ cycloalkene.

In the present specification, examples of the "$C_{6-14}$ aromatic hydrocarbon ring" include benzene and naphthalene.

In the present specification, examples of the "$C_{3-10}$ cycloalkane" include cyclopropane, cyclobutane, cyclopentane, cyclohexane, cycloheptane and cyclooctane.

In the present specification, examples of the "$C_{3-10}$ cycloalkene" include cyclopropene, cyclobutene, cyclopentene, cyclohexene, cycloheptene and cyclooctene.

In the present specification, examples of the "heterocycle" include an aromatic heterocycle and a non-aromatic heterocycle, each containing, as a ring-constituting atom besides carbon atom, 1 to 4 hetero atoms selected from a nitrogen atom, a sulfur atom and an oxygen atom.

In the present specification, examples of the "aromatic heterocycle" include a 5- to 14-membered (preferably 5- to 10-membered) aromatic heterocycle containing, as a ring-constituting atom besides carbon atom, 1 to 4 hetero atoms selected from a nitrogen atom, a sulfur atom and an oxygen atom. Preferable examples of the "aromatic heterocycle" include 5- or 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; and 8- to 14-membered fused polycyclic (preferably bi or tricyclic) aromatic heterocycles such as benzothiophene, benzofuran, benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiin, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxazine and the like.

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms selected from a nitrogen atom, a sulfur atom and an oxygen atom. Preferable examples of the "non-aromatic heterocycle" include 3- to 8-membered monocyclic non-aromatic heterocycles such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepanine, diazepane, azepine, azocane, diazocane, oxepane and the like; and 9- to 14-membered fused polycyclic (preferably bi or tricyclic) non-aromatic heterocycles such as dihydrobenzofuran, dihydrobenzimidazole, dihydrobenzoxazole, dihydrobenzothiazole, dihydrobenzisothiazole, dihydronaphtho[2,3-b]thiophene, tetrahydroisoquinoline, tetrahydroquinoline, 4H-quinolizine, indoline, isoindoline, tetrahydrothieno[2,3-c]pyridine, tetrahydrobenzazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydrothioxanthene, octahydroisoquinoline and the like.

In the present specification, examples of the "nitrogen-containing heterocycle" include a "heterocycle" containing at least one nitrogen atom as a ring-constituting atom.

In the present specification, examples of the "$C_{1-4}$ alkyl group" include the alkyl group which number of the carbon atom is one or four among those exemplified in the above $C_{1-6}$ alkyl group.

In the present specification, examples of the "$C_{4-10}$ alkyl group" include the alkyl group which number of the carbon atom is four or more among those exemplified in the above $C_{1-6}$ alkyl group, and heptyl, octyl, nonyl, decyl.

In the present specification, examples of the "$C_{1-6}$ alkylene group" include —CH₂—, —(CH₂)₂—, —(CH₂)₃—, —(CH₂)₄—, —(CH₂)₅—, —(CH₂)₆—, —CH(CH₃)—, —C(CH₃)₂—, —CH(C₂H₅)—, —CH(C₃H₇)—, —CH(CH(CH₃)₂)—, —(CH(CH₃))₂—, —CH₂—CH(CH₃)—, —CH(CH₃)—CH₂—, —CH₂—CH₂—C(CH₃)₂—, —C(CH₃)₂—CH₂—CH₂—, —CH₂—CH₂—CH₂—C(CH₃)₂—, —C(CH₃)₂—CH₂—CH₂—CH₂—.

In the present specification, "an optionally substituted $C_{4-10}$ alkyl group" include a $C_{4-10}$ alkyl group optionally having substituent(s) selected from the above substituent group A.

In the present specification, "an optionally substituted $C_{1-6}$ alkylene group" include a $C_{1-6}$ alkylene group having substituent(s) selected from the above substituent group A.

In the present specification, "an optionally substituted methine group" include a methine group optionally having substituent(s) selected from the above substituent group A.

In the present specification, "an optionally substituted methylene group" include a methylene group having substituent(s) selected from the above substituent group A.

Preferable examples of $R^1$, $R^2$, $R^3$, $R^4$, $R^5$, $Z^-$, X, $Y^A$, $Y^B$, $Y^C$, $L^A$, $L^B$, $L^C$, $R^{A1}$, $R^{A2}$, $R^{B1}$, $R^{B2}$, $R^{C1}$ and $R^{C2}$ in the compound represented by the above mentioned general formula are recited below.

$R^1$ is preferably a $C_{1-4}$ alkyl group and more preferably a methyl group.

$R^2$ is preferably a $C_{1-4}$ alkyl group and more preferably a methyl group.

$R^3$ is preferably a methyl group.

$R^4$ is preferably a methyl group.

$R^5$ is preferably a methyl group.

As $Z^-$ a pharmaceutically acceptable negative ion is preferable, of which suitable examples that can be recited are: a halide ion (a fluoride ion, chloride ion, bromide ion and iodide ion); an inorganic acid negative ion selected from a group consisting of a nitrate ion, sulfate ion, phosphate ion; an organic acid negative ion selected from a group consisting of a formate ion, acetate ion, trifluoroacetate ion, phthalate ion, fumarate ion, oxalate ion, tartrate ion, malate ion, citrate ion, succinate ion, maleate ion, methanesulfonate ion, benzenesulfonate ion, p-toluenesulfonate ion; and an acidic amino acid negative ion selected from a group consisting of an aspartate ion and glutamate ion. $Z^-$ is more preferably a halide ion (in particular, an iodide ion).

X is preferably a $C_{1-6}$ alkylene group and more preferably an ethylene group, trimethylene group or tetramethylene group.

$Y^A$ is preferably a methine group.
$Y^B$ is preferably a methine group.
$Y^C$ is preferably a methine group.
$L^A$ is preferably a bond or methylene group.
$L^B$ is preferably a bond or methylene group.
$L^C$ is preferably a bond or methylene group.
$R^{A1}$ is preferably a $C_{4-10}$ alkyl group and more preferably a butyl group, pentyl group or hexyl group.
$R^{A2}$ is preferably a $C_{4-10}$ alkyl group and more preferably a butyl group, pentyl group or hexyl group.
$R^{B1}$ is preferably a $C_{4-10}$ alkyl group and more preferably a butyl group, pentyl group or hexyl group.
$R^{B2}$ is preferably a $C_{4-10}$ alkyl group and more preferably a butyl group, pentyl group or hexyl group.
$R^{C1}$ is preferably a $C_{4-10}$ alkyl group and more preferably a butyl group, pentyl group or hexyl group.
$R^{C2}$ is preferably a $C_{4-10}$ alkyl group and more preferably a butyl group, pentyl group or hexyl group.

As suitable examples of compound (I), the following can be recited:
Compound (A):
Compound (I) wherein
$R^1$, $R^2$, $R^3$, $R^4$ and $R^5$ are a methyl group;
$Z^-$ is a halide ion (in particular, an iodide ion);
X is an ethylene group, trimethylene group or a tetramethylene group;
$Y^A$, $Y^B$ and $Y^C$ are a methine group;
$L^A$, $L^B$ and $L^C$, independently from each other, are a bond or methylene group;
$R^{A1}$, $R^{A2}$, $R^{B1}$, $R^{B2}$, $R^{C1}$ and $R^{C2}$, independently from each other, are a butyl group, pentyl group or hexyl group.
Compound (B):
Compound (A) wherein W is formula —$NR^1R^2$.
Compound (C):
Compound (A) wherein
W is formula —$N^+R^3R^4R^5(Z^-)$;
$Z^-$ is an iodide ion;
X is a tetramethylene group;
$R^{A1}$, $R^{A2}$, $R^{B1}$, $R^{B2}$, $R^{C1}$ and $R^{C2}$ are a pentyl group.

The salt of compound (I) is preferably a pharmacologically acceptable salt. Examples thereof include salts with inorganic bases, salts with organic bases, salts with inorganic acids, salts with organic acids and salts with basic or acidic amino acids.

Preferred examples of salts with inorganic bases include: alkali metal salts such as sodium salt and potassium salt; alkaline earth metal salts such as calcium salt and magnesium salt; and aluminum salt and ammonium salt.

Preferred examples of salts with organic bases include salts with trimethylamine, triethylamine, pyridine, picoline, ethanolamine, diethanolamine, triethanolamine, tromethamine [tris(hydroxymethyl)methylamine], tert-butylamine, cyclohexylamine, benzylamine, dicyclohexylamine or N,N-dibenzylethylenediamine.

Preferred examples of salts with inorganic acids include salts with hydrofluoric acid, hydrochloric acid, hydrobromic acid, hydroiodic acid, nitric acid, sulfuric acid or phosphoric acid.

Preferred examples of salts with organic acids include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid or p-toluenesulfonic acid.

Preferred examples of salts with basic amino acids include salts with arginine, lysine or ornithine.

Preferred examples of salts with acidic amino acids include salts with aspartic acid or glutamic acid.

"Active ingredient" used in the present invention signifies a substance having biological or pharmacologically activity, signifying, in particular, substances useful for pharmaceutical use or research-aiming use. As an active ingredient, for example, nucleic acids can be recited.

"Nucleic acid" may be any molecule, as far as it is a nucleotide or a molecule resulting from polymerization of a nucleotide or a molecule functionally equivalent to the nucleotide; for example, RNA, which is a ribonucleotide polymer, DNA, which is a deoxyribonucleotide polymer, a mixed polymer of a ribonucleotide and deoxyribonucleotide, and a nucleotide polymer, including a nucleotide analogue, can be mentioned; furthermore, the nucleic acid may be a nucleotide polymer comprising a nucleic acid derivative. In addition, the nucleic acid may be a single-stranded nucleic acid or double-stranded nucleic acid. Double-stranded nucleic acids comprise double-stranded nucleic acids wherein one strand hybridizes with the other strand under stringent conditions.

The nucleotide analogue may be any molecule, as far as it is a molecule prepared by modifying a ribonucleotide, a deoxyribonucleotide, RNA or DNA in order to improve the nuclease resistance thereof, to stabilize the same, to increase the affinity thereof for a complementary chain nucleic acid, to increase the cell permeability thereof, or to visualize the same, compared with the RNA or DNA. The nucleotide analogue may be a naturally existing molecule or non-natural molecule; for example, a nucleotide analogue modified at the sugar moiety thereof, a nucleotide analogue modified at phosphoric acid diester bond etc. can be recited.

The nucleotide analogue modified at the sugar moiety thereof may be any one, as far as any optional chemical structural substance has been added to or substituted for a portion or all of the chemical structure of the sugar of the nucleotide; examples thereof which can be recited are a nucleotide analogue substituted by 2'-O-methylribose, a nucleotide analogue substituted by 2'-O-propylribose, a nucleotide analogue substituted by 2'-methoxyethoxyribose, a nucleotide analogue substituted by 2'-O-methoxyethylribose, a nucleotide analogue substituted by 2'-O-[2-(guanidium)ethyl]ribose, a nucleotide analogue substituted by 2'-O-fluororibose, a bridged nucleic acid (BNA) having two cyclic structures as a result of introduction of a bridging structure into the sugar moiety, more specifically a locked nucleic acid (LNA) wherein the oxygen atom at the 2' position and the carbon atom at the 4' position have been bridged via methylene, and an ethylene bridged nucleic acid) (ENA) [Nucleic Acid Research, 32, e175 (2004)]. In addition, a peptide nucleic acid (PNA) [Acc. Chem. Res., 32, 624 (1999)], an oxypeptide nucleic acid (OPNA) [J. Am. Chem. Soc., 123, 4653 (2001)], and a peptide ribonucleic acid (PRNA) [J. Am. Chem. Soc., 122, 6900 (2000)] etc. can be recited.

The nucleotide analogue modified at phosphoric acid diester bond may be any one, as far as any optional chemical substance has been added to, or substituted for, a portion or all of the chemical structure of the phosphoric acid diester bond of the nucleotide; examples thereof which can be recited are a nucleotide analogue substituted by a phosphorothioate bond, a nucleotide analogue substituted by an N3'-P5' phosphoamidate bond [SAIBO KOGAKU, 16, 1463-1473 (1997)] [RNAi Method and Antisense Method, Kodansha (2005)] etc.

The nucleic acid derivative may be any molecule, as long as it is a molecule prepared by adding another chemical substance to the nucleic acid in order to improve the nuclease resistance thereof, to stabilize the same, to increase the affinity thereof for a complementary chain nucleic acid, to increase the cell permeability thereof, or to visualize the same, compared with the nucleic acid; examples thereof which can be recited are a 5'-polyamine conjugated derivative, a cholesterol conjugated derivative, a steroid conjugated derivative, a bile acid conjugated derivative, a vitamin conjugated derivative, a Cy5 conjugated derivative, a Cy3 conjugated derivative, a 6-FAM conjugated derivative, a biotin conjugated derivative etc.

The active ingredient is preferably a nucleic acid; as specific examples of the nucleic acid, siRNA, miRNA, miRNA mimic, antisense oligonucleotide, ribozyme, mRNA, decoy nucleic acid, aptamer active ingredient can be, for example, recited. As the nucleic acid, siRNA or mRNA is preferable.

In the present invention, "siRNA" is a double-strand RNA having 10 to 30 bases, preferably 15 to 20 bases, or an analogue thereof, meaning those having a complementary sequence as well. The si RNA preferably has at the 3' terminal 1 to 3 bases, more preferably an overhang of two bases. The complementary sequence portion may be completely complementary or may comprise a non-complementary base; the complementary sequence part preferably is completely complementary.

In the present invention, "mRNA" means an RNA comprising a base sequence translatable into a protein.

In the present invention, compound (I) can be used as a cationic lipid. A cationic lipid can, in a solvent or suspension medium, a complex with plural molecules. In the above mentioned complex, in addition to compound (I), another component may be comprised. As examples of the above mentioned another component, other lipids (structure lipids (e.g. cholesterol and phosphatidylcholine (e.g. dipalmytoyl-phosphatidylcholine or distearoyl phosphatidylcholine)), a polyethyleneglycol lipid (e.g. GM-020 (NOF CORPORATION), GS-020 (NOF CORPORATION) etc.)) and an active ingredient can be recited.

In the present invention, "lipid particle" means a complex included in the above mentioned complex but not comprising an active ingredient.

(1)(i) The present inventive compound or (ii) the lipid particle containing said compound can be, as a composition with (2) an active ingredient and (3) if necessary, the above mentioned other lipids, used for a medicament or agent (in the present description, such composition may be abbreviated as the present inventive composition). The present inventive composition can be produced, using a pharmacologically acceptable carrier, with a method known per se in the technical field of formulation. As a formulation of the above mentioned medicament, for example, a formulation for parenteral administration (e.g. a liquid formulation such as an injection) blended with conventional additive such as a buffer and/or stabilizer, and topical formulation blended with a conventional carrier for medicaments such as an ointment, cream, liquid or plaster etc.

The present inventive composition can be used for introducing an active ingredient into many kinds of cells, tissues or organs. As these cells, tissues or organs, the following are, for example, recited: splenocytes, nerve cells, glial cells, pancreace β cell, bone marrow cells, mesangial cells, Langerhans' cells, epidermic cells, epithelial cells, endothelial cells, fibroblasts, fibrocytes, myocyte, adipocyte, immune cells (e.g. macrophages, T cells, B cells, natural killer cells, mast cells, neutrophils, basophils, eosinophils, monocytes), megakaryocytes, synovial cells, chondrocytes, bone cells, osteoblasts, osteoclasts, mammary gland cells, hepatocytes or interstitial cells; or precursor cells of these cells, stem cells etc. or hematopoietic cells; or any tissues or organs where these cells exist, i.e., for example, brain or any of brain regions (e.g. olfactory bulb, amygdaloid nucleus, basal ganglia, hippocampus, thalamus, hypothalamus, subthalamic nucleus, cerebral cortex, medulla oblongata, cerebellum, occipital pole, frontal lobe, temporal lobe, putamen, caudate nucleus, corpus callosum, substantia nigra), spinal cord, hypophysis, stomach, pancreas, kidney, liver, gonad, thyroid, gall-bladder, bone marrow, adrenal gland, skin, muscle, lung, gastrointestinal tract (e.g. large intestine and small intestine), blood vessel, heart, thymus, spleen, submandibular gland, peripheral blood, peripheral blood cells, prostate, testicles, testis, ovary, placenta, uterus, bone, joint, skeletal muscle. These cells tissues or organs may be cancerated cancer cells or cancer tissues etc.

The present inventive composition is excellent, in particular, in efficiency for introducing an active ingredient into liver, cancer cells, adipocyte, hematopoietic cells or bone marrow cells.

The present inventive compound and present inventive composition can be used stably as well as safely with low toxicity. In using the present inventive composition as a medicament, the composition can be administered in such a manner that the active ingredient be administered at an effective amount in the administration target (e.g. mammals such as humans).

Production methods for the present inventive compounds are explained hereinbelow.

A starting material or a reagent used in each step in the production method given below, as well as the obtained compound, may each form a salt. As such salts, those similar to the aforementioned salts of the present inventive compound can be recited.

When the compound obtained in each step is a free compound, this compound can be converted to a salt of interest by a method known per se in the art. On the contrary, when the compound obtained in each step is a salt, this salt can be converted to a free form or another type of salt of interest by a method known per se in the art.

The compound obtained in each step may be used in the next reaction in the form of its reaction solution or after being obtained as a crude product. Alternatively, the compound obtained in each step can be isolated and/or purified from the reaction mixture by a separation approach such as concentration, crystallization, recrystallization, distillation, solvent extraction, fractionation, or chromatography according to a routine method.

If a starting material or a reagent compound for each step is commercially available, the commercially available product can be used directly.

In the reaction of each step, the reaction time can differ depending on the reagent or the solvent used and is usually 1 minute to 48 hours, preferably 10 minutes to 8 hours, unless otherwise specified.

In the reaction of each step, the reaction temperature can differ depending on the reagent or the solvent used and is usually −78° C. to 300° C., preferably −78° C. to 150° C., unless otherwise specified.

In the reaction of each step, the pressure can differ depending on the reagent or the solvent used and is usually 1 atm to 20 atm, preferably 1 atm to 3 atm, unless otherwise specified.

In the reaction of each step, for example, a microwave synthesis apparatus such as a Biotage Initiator may be used. The reaction temperature can differ depending on the reagent or the solvent used and is usually room temperature to 300° C., preferably 50° C. to 250° C., unless otherwise specified. The reaction time can differ depending on the reagent or the solvent used and is usually 1 minute to 48 hours, preferably 1 minute to 8 hours, unless otherwise specified.

In the reaction of each step, the reagent is used at 0.5 equivalents to 20 equivalents, preferably 0.8 equivalents to 5 equivalents, with respect to the substrate, unless otherwise specified. In the case of using the reagent as a catalyst, the reagent is used at 0.001 equivalents to 1 equivalent, preferably 0.01 equivalents to 0.2 equivalents, with respect to the substrate. When the reagent also serves as a reaction solvent, the reagent is used in the amount of the solvent.

In each step of a reaction, the reaction is carried out without a solvent or by dissolution or suspension in an appropriate solvent, unless otherwise specified. Specific examples of solvents that may be used include solvents described in the Examples and those given below:

alcohols such as methanol, ethanol, tert-butyl alcohol and 2-methoxyethanol;
ethers such as diethyl ether, diphenyl ether, tetrahydrofuran and 1,2-dimethoxyethane;
aromatic hydrocarbons such as chlorobenzene, toluene and xylene;
saturated hydrocarbons such as cyclohexane and hexane;
amides such as N,N-dimethylformamide and N-methylpyrrolidone;
halogenated hydrocarbons such as dichloromethane and carbon tetrachloride;
nitriles such as acetonitrile;
sulfoxides such as dimethyl sulfoxide;
aromatic organic bases such as pyridine;
acid anhydrides such as acetic anhydride;
organic acids such as formic acid, acetic acid and trifluoroacetic acid;
inorganic acids such as hydrochloric acid and sulfuric acid;
esters such as ethyl acetate;
ketones such as acetone and methyl ethyl ketone; and
water.

Two or more of these solvents may be used as a mixture at an appropriate ratio.

In each reaction step making use of a base, examples of bases that may be used are those given in the Examples or listed below:

inorganic bases such as sodium hydroxide and magnesium hydroxide;
basic salts such as sodium carbonate, potassium carbonate and sodium bicarbonate;
organic bases such as triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole and piperidine;
metal alkoxides such as sodium ethoxide and potassium tert-butoxide;
alkali metal hydrides such as sodium hydride;
metal amides such as sodium amide, lithium diisopropylamide and lithium hexamethyldisilazide; and
organolithium reagents such as n-butyllithium.

In each reaction step making use of an acid or acid catalyst, examples of acids or acid catalysts that may be used are those given in the Examples or listed below:

inorganic acids such as hydrochloric acid, sulfuric acid, nitric acid, hydrobromic acid and phosphoric acid;
organic acids such as acetic acid, trifluoroacetic acid, citric acid, p-toluenesulfonic acid and 10-camphorsulfonic acid; and
Lewis acids such as boron trifluoride-diethyl ether complex, zinc iodide, anhydrous aluminum chloride, anhydrous zinc chloride and anhydrous iron chloride.

Unless stated otherwise, each reaction step may be carried out according to a method given in the Examples or a standard method known per se in the art, such as those described in Jikken Kagaku Koza (Encyclopedia of Experimental Chemistry in English), 5th Ed., Vol. 13 to Vol. 19 (edited by the Chemical Society of Japan); Shin Jikken Kagaku Koza (New Encyclopedia of Experimental Chemistry in English), Vol. 14 to Vol. 15 (edited by the Chemical Society of Japan); Reactions and Syntheses: In the Organic Chemistry Laboratory, 2th Ed. Revised (L. F. Tietze, Th. Eicher, Nankodo); Organic Name Reactions; The Reaction Mechanism and Essence, Revised (Hideo Togo, Kodansha); Organic Syntheses Collective Volume I-VII (John Wiley & Sons, Inc.); Modern Organic Synthesis in the Laboratory: A Collection of Standard Experimental Procedures (Jie Jack Li, Oxford University Press); Comprehensive Heterocyclic Chemistry III, Vol. 1 to Vol. 14 (Elsevier Japan KK); Strategic Applications of Named Reactions in Organic Synthesis (translated by Kiyoshi Tomioka, Kagaku-Dojin Publishing); Comprehensive Organic Transformations (VCH Publishers, Inc.), 1989; etc.

In each step, the protection or deprotection reaction of a functional group may be carried out according to a method described in the Examples or a method known per se in the art, for example, a method described in "Protective Groups in Organic Synthesis, 4th Ed." (Theodora W. Greene, Peter G. M. Wuts), Wiley-Interscience, 2007; "Protecting Groups, 3rd Ed." (P. J. Kocienski) Thieme, 2004); etc.

Examples of a protective group for a hydroxy group or a phenolic hydroxy group in alcohols or the like include: ether-type protective groups such as methoxymethyl ether, benzyl ether, t-butyldimethylsilyl ether and tetrahydropyranyl ether; carboxylic acid ester-type protective groups such as acetic acid ester; sulfonic acid ester-type protective groups such as methanesulfonic acid ester; and carbonic acid ester-type protective groups such as t-butyl carbonate.

Examples of a protective group for a carbonyl group in aldehydes include: acetal-type protective groups such as dimethylacetal; and cyclic acetal-type protective groups such as cyclic 1,3-dioxane.

Examples of a protective group for a carbonyl group in ketones include: ketal-type protective groups such as dimethylketal; cyclic ketal-type protective groups such as cyclic 1,3-dioxane; oxime-type protective groups such as O-methyloxime; and hydrazone-type protective groups such as N,N-dimethylhydrazone.

Examples of a protective group for a carboxyl group include: ester-type protective groups such as methyl ester; and amide-type protective groups such as N,N-dimethylamide.

Examples of a protective group for thiol include: ether-type protective groups such as benzyl thioether; and ester-type protective groups such as thioacetic acid ester, thiocarbonate and thiocarbamate.

Examples of a protective group for an amino group or aromatic heterocycle such as imidazole, pyrrole or indole include: carbamate-type protective groups such as benzyl carbamate; amide-type protective groups such as acetamide;

alkylamine-type protective groups such as N-triphenylmethylamine; and sulfonamide-type protective groups such as methanesulfonamide.

These protective groups can be removed by use of a method known per se in the art, for example, a method using an acid, a base, ultraviolet light, hydrazine, phenylhydrazine, sodium N-methyldithiocarbamate, tetrabutylammonium fluoride, palladium acetate or trialkylsilyl halide (for example, trimethylsilyl iodide or trimethylsilyl bromide), or a reduction method.

In each step making use of a reduction reaction, examples of reducing agents that may be used include: metal hydrides such as lithium aluminum hydride, sodium triacetoxyborohydride, sodium cyanoborohydride, diisobutyl aluminum hydride (DIBAL-H), sodium borohydride and tetramethylammonium triacetoxyborohydride; boranes such as borane-tetrahydrofuran complex; Raney nickel; Raney cobalt; hydrogen; and formic acid. In the case of reducing a carbon-carbon double bond or triple bond, a method using a catalyst such as palladium-carbon or Lindlar's catalyst may be used.

In each step making use of an oxidation reaction, examples of oxidizing agents that may be used include: peracids such as m-chloroperbenzoic acid (MCPBA), hydrogen peroxide and t-butyl hydroperoxide; perchlorates such as tetrabutylammonium perchlorate; chlorates such as sodium chlorate; chlorites such as sodium chlorite; periodates such as sodium periodate; high-valent iodine reagents such as iodosylbenzene; manganese reagents, such as manganese dioxide and potassium permanganate; lead reagents such as lead tetraacetate; chromium reagents, such as pyridinium chlorochromate (PCC), pyridinium dichromate (PDC) and Jones' reagent; halogen reagents such as N-bromosuccinimide (NBS); oxygen; ozone; sulfur trioxide-pyridine complex; osmium tetraoxide; selenium dioxide; and 2,3-dichloro-5,6-dicyano-1,4-benzoquinone (DDQ).

In each step making use of a radical cyclization reaction, examples of radical initiators that may be used include: azo compounds such as azobisisobutyronitrile (AIBN); water-soluble radical initiators such as 4-4'-azobis-4-cyanopentanoic acid (ACPA); triethylboron in the presence of air or oxygen; and benzoyl peroxide. Examples of radical initiators that may be used include tributylstannane, tristrimethylsilylsilane, 1,1,2,2-tetraphenyldisilane, diphenylsilane and samarium iodide.

In each step making use of a Wittig reaction, examples of Wittig reagents that may be used include alkylidenephosphoranes. The alkylidenephosphoranes can be prepared by a method known per se in the art, for example, the reaction between a phosphonium salt and a strong base.

In each step making use of a Horner-Emmons reaction, examples of reagents that may be used include phosphonoacetic acid esters such as methyl dimethylphosphonoacetate and ethyl diethylphosphonoacetate, and bases such as alkali metal hydrides and organic lithiums.

In each step making use of a Friedel-Crafts reaction, examples of reagents that may be used include a Lewis acid and an acid chloride or alkylating agent (e.g. alkyl halides, alcohols and olefins). Alternatively, an organic or inorganic acid may be used instead of the Lewis acid, and acid anhydrides such as acetic anhydride may be used instead of the acid chloride.

In each step making use of an aromatic nucleophilic substitution reaction, a nucleophile (e.g., amine or imidazole) and a base (e.g., basic salt or organic base) may be used as reagents.

In each step making use of a nucleophilic addition reaction using a carbanion, nucleophilic 1,4-addition reaction (Michael addition reaction) using a carbanion, or nucleophilic substitution reaction using a carbanion, examples of bases that may be used for generating the carbanion include organolithium reagents, metal alkoxides, inorganic bases and organic bases.

In each step making use of a Grignard reaction, examples of Grignard reagents that may be used include aryl magnesium halides such as phenyl magnesium bromide, and alkyl magnesium halides such as methyl magnesium bromide. The Grignard reagent can be prepared by a method known per se in the art, for example, the reaction between an alkyl halide or aryl halide and magnesium metal in ether or tetrahydrofuran as a solvent.

In each step making use of a Knoevenagel condensation reaction, an active methylene compound flanked by two electron-attracting groups (e.g., malonic acid, diethyl malonate or malononitrile) and a base (e.g., organic bases, metal alkoxides or inorganic bases) may be used as reagents.

In each step making use of a Vilsmeier-Haack reaction, phosphoryl chloride and an amide derivative (e.g. N,N-dimethylformamide) may be used as reagents.

In each step making use of an azidation reaction of alcohols, alkyl halides or sulfonic acid esters, examples of azidating agents that may be used include diphenylphosphorylazide (DPPA), trimethylsilylazide and sodium azide. In the case of azidating, for example, alcohols, a method using diphenylphosphorylazide and 1,8-diazabicyclo[5,4,0]undec-7-ene (DBU), a method using trimethylsilylazide and Lewis acid, or the like can be used.

In each step making use of a reductive amination reaction, examples of reducing agents that may be used include sodium triacetoxyborohydride, sodium cyanoborohydride, hydrogen and formic acid. When the substrate is an amine compound, examples of carbonyl compounds that may be used include p-formaldehyde as well as aldehydes such as acetaldehyde and ketones such as cyclohexanone. When the substrate is a carbonyl compound, examples of amines that may be used include primary amines such as ammonia and methylamine, and secondary amines such as dimethylamine.

In each step making use of a Mitsunobu reaction, azodicarboxylic acid esters (e.g. diethyl azodicarboxylate (DEAD) and diisopropyl azodicarboxylate (DIAD)) and triphenylphosphine may be used as reagents.

In each step making use of an esterification, amidation or ureation reaction, examples of reagents that may be used include acyl halides such as acid chlorides or acid bromides, and activated carboxylic acids such as acid anhydrides, active esters or sulfate esters. Examples of the activating agents for carboxylic acids include: carbodiimide condensing agents such as 1-ethyl-3-(3-dimethylaminopropyl)carbodiimide hydrochloride (WSCD); triazine condensing agents such as 4-(4,6-dimethoxy-1,3,5-triazin-2-yl)-4-methylmorpholinium chloride-n-hydrate (DMT-MM); carbonic acid ester condensing agents such as 1,1-carbonyldiimidazole (CDI); diphenylphosphorylazide (DPPA); benzotriazol-1-yloxy-trisdimethylaminophosphonium salt (BOP reagent); 2-chloro-1-methyl-pyridinium iodide (Mukaiyama reagent); thionyl chloride; lower alkyl haloformate such as ethyl chloroformate; O-(7-azabenzotriazol-1-yl)-N,N,N',N'-tetramethyluronium hexafluorophosphate (HATU); sulfuric acid; and combinations thereof. In the case of using a carbodiimide condensing agent, the addition of an additive such as 1-hydroxybenzotriazole (HOBt), N-hydroxysuccinimide (HOSu) or dimethylaminopyridine (DMAP) to the reaction may be beneficial.

In each step making use of a coupling reaction, examples of metal catalysts that may be used include palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocene palladium(II) chloride and palladium(II) acetate; nickel compounds such as tetrakis(triphenylphosphine)nickel(0); rhodium compounds such as tris(triphenylphosphine)rhodium(III) chloride; cobalt compounds; copper compounds such as copper oxide and copper(I) iodide; and platinum compounds. Addition of a base to the reaction may also be beneficial. Examples of such bases include inorganic bases and basic salts. 1

In each step making use of a thiocarbonylation reaction, diphosphorus pentasulfide is typically used as a thiocarbonylating agent. A reagent having a 1,3,2,4-dithiadiphosphetane-2,4-disulfide structure such as 2,4-bis(4-methoxyphenyl-1,3,2,4-dithiadiphosphetane-2,4-disulfide (Lawesson reagent) may be used instead of diphosphorus pentasulfide.

In each step making use of a Wohl-Ziegler reaction, examples of halogenating agents that may be used include N-iodosuccinimide, N-bromosuccinimide (NBS), N-chlorosuccinimide (NCS), bromine and sulfuryl chloride. The reaction can be accelerated by the further addition of a radical initiator such as heat, light, benzoyl peroxide or azobisisobutyronitrile.

In each step making use of a halogenation reaction of a hydroxy group, examples of halogenating agents that may be used include a hydrohalic acid or the acid halide of an inorganic acid; examples include hydrochloric acid, thionyl chloride, and phosphorus oxychloride for chlorination and 48% hydrobromic acid for bromination. In addition, a method for obtaining an alkyl halide from an alcohol by the action of triphenylphosphine and carbon tetrachloride or carbon tetrabromide, etc., may also be used. Alternatively, a method for synthesizing an alkyl halide through a 2-step reaction involving the conversion of an alcohol to a sulfonic acid ester and subsequent reaction with lithium bromide, lithium chloride or sodium iodide may also be used.

In each step making use of an Arbuzov reaction, examples of reagents that may be used include alkyl halides such as bromoethyl acetate, and phosphites such as triethylphosphite and tri(isopropyl)phosphite.

In each step making use of a sulfone-esterification reaction, examples of the sulfonylating agent used include methanesulfonyl chloride, p-toluenesulfonyl chloride, methanesulfonic anhydride and p-toluenesulfonic anhydride.

In each step making use of a hydrolysis reaction, an acid or a base may be used as a reagent. In the case of carrying out the acid hydrolysis reaction of a t-butyl ester, reagents such as formic acid, triethylsilane or the like may be added to reductively trap the by-product t-butyl cation.

In each step making use of a dehydration reaction, examples of dehydrating agents that may be used include sulfuric acid, diphosphorus pentaoxide, phosphorus oxychloride, N,N'-dicyclohexylcarbodiimide, alumina and polyphosphoric acid.

Compound (I) can be produced, for example, with Production method A below.
(Production Method A)

[chem 2]

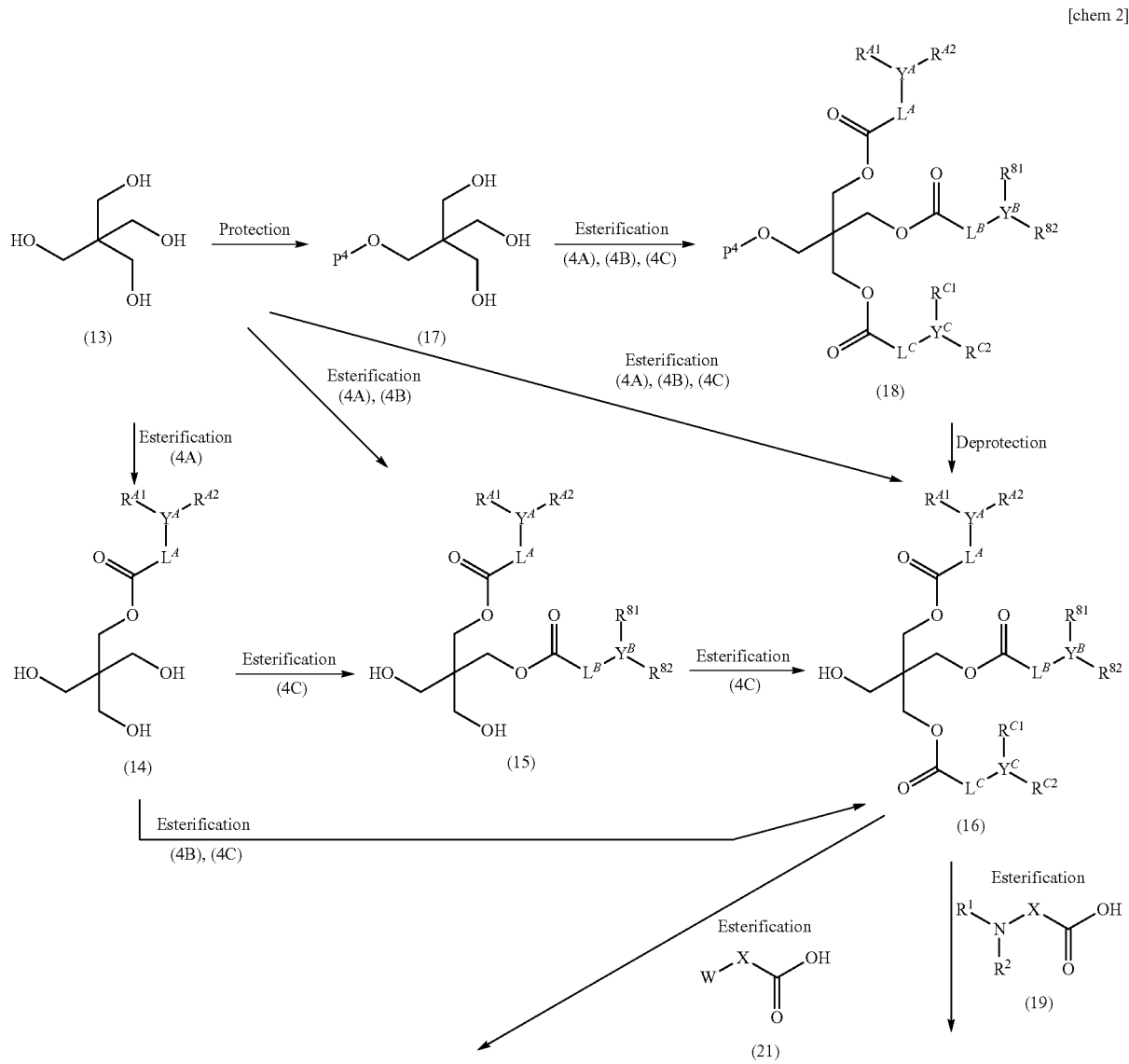

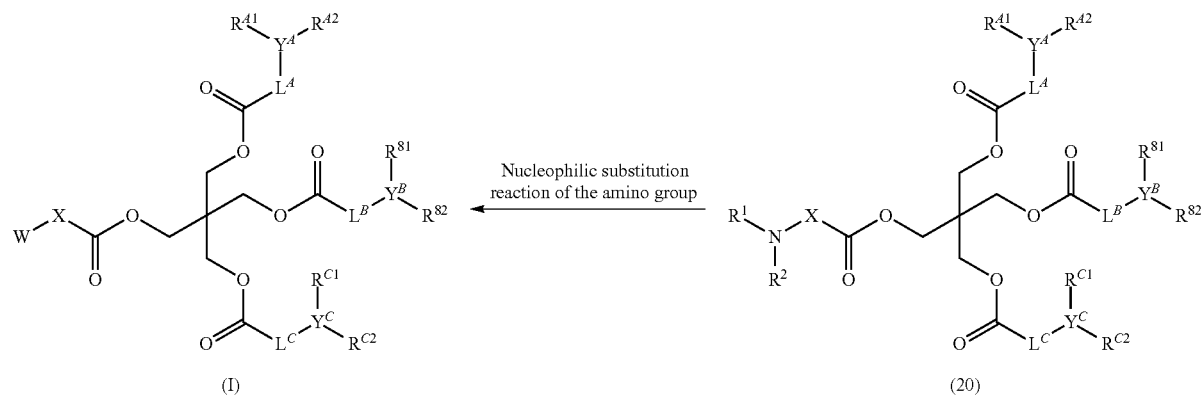

(I)                                               (20)

[In the scheme, $P^4$ represents a protective group, compound (4A) is represented by a formula:

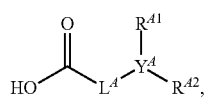

compound (4B) is represented by a formula:

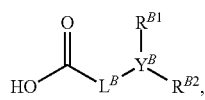

compound (4C) is represented by a formula:

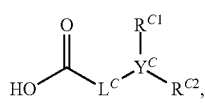

and the other symbols denote the same meaning as describes above.]

As the protective group represented by $P^4$, the protective group for a hydroxyl group above described is used.

Compound (16) can be produced by removing the protective group from compound (18). For removing the protective group, tetra-n-butylammonium fluoride and an acid in combination can be used.

Compound (I) can also be produced with a nucleophilic substitution reaction of the amino group in compound (20). As an example of the agent used for the above identified nucleophilic substitution reaction, alkyl halides can be recited.

Compound (4A) used in the aforementioned Production method A can be produced with compound (1) or compound (7) via, for example, Production method B described below.

(Production Method B)

[chem 3]

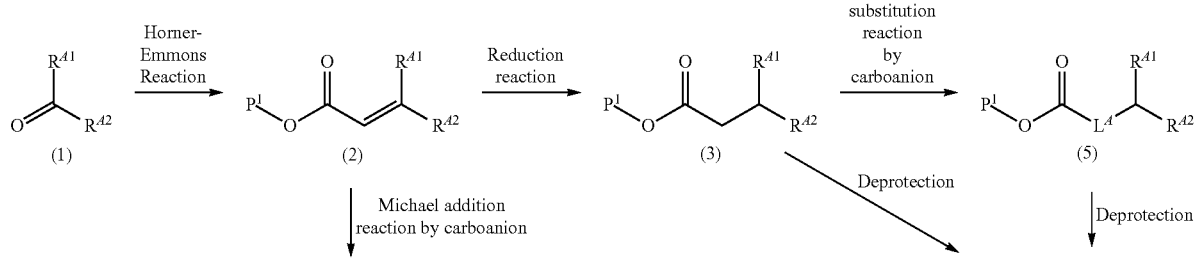

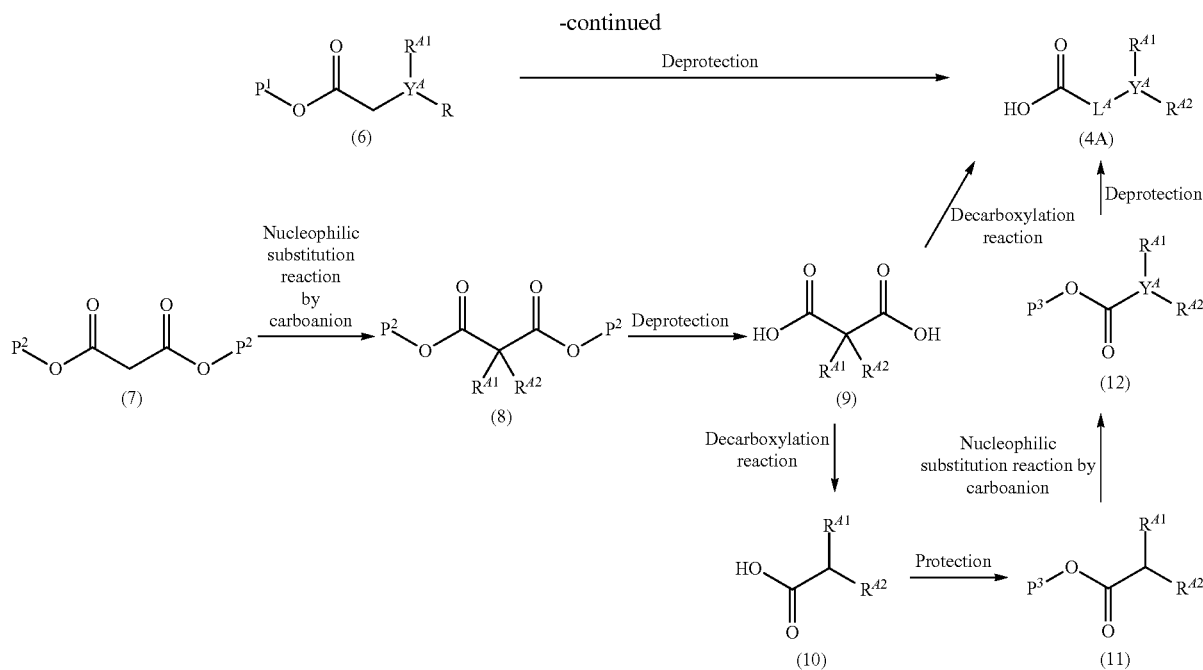

[In the scheme, $P^1$, $P^2$ and $P^3$ each independently represent a protective group, and the other symbols denote the same meaning as described above.]

As the protective groups represented by $P^1$, $P^2$ and $P^3$, the protective group for the carboxyl group as described above is used.

Compound (4A) and compound (10) can also be produced with a decarboxylation reaction on compound (9). Reaction temperature, which may vary depending on the agent or solvent used, normally is room temperature to 300° C., and preferably 50° C. to 250° C. In the decarboxylation reaction, an acid can be used.

Compound (5) can be produced with a nucleophilic substitution reaction on compound (3) with a carboanion. As examples of the agent used in the nucleophilic substitution reaction, alkyl halides and fluorinating agent (e.g. N-fluorobenzenesulfoneimide, 3,3-dimethyl-1-(trifluoromethyl)-1,2-benziodoxol) can be recited.

Compound (6) can be produced with a Michael addition reaction on compound (2) with a carboanion. As examples of the agent used in the addition reaction, organocoppers (can be prepared by reacting a Grignard agent or organolithium agent with a copper halide) can be recited. In addition, as the above mentioned agent, an agent which combines an organocopper agent with an acid or trimethylsilyl chloride can be used.

Compound (8) can be produced with a nucleophilic substitution reaction on compound (7) with a carboanion. As examples of the agent used in the nucleophilic substitution reaction, alkyl halides can be recited.

Compound (12) can be produced with a nucleophilic substitution reaction on compound (11) with a carboanion. As examples of the agent used in the nucleophilic substitution reaction, alkyl halides can be recited.

Compounds (4B) and (4C) used in the production method A can also be produced in a similar manner as compound (4A).

A production method of the lipid particles and compositions comprising the present inventive compound are explained hereinbelow.

The lipid particles can be produced by dissolving the present inventive compound in an organic solvent after mixing with another lipid component and mixing the obtained organic solvent solution with water or a buffer solution as a lipid particle suspension. The above mentioned mixing can be conducted using a micro fluid mixing system (e.g. Asia microfluidic system (Syrris)). The obtained lipid particles may be subject to dialysis or sterile filtration.

As the aforementioned "another lipid component", for example, structure lipids (e.g. cholesterol and phosphatidylcholine (e.g. dipalmytoylphosphatidylcholine, distearoyl phosphatidylcholine)), and polyethyleneglycol lipid (e.g. GM-020 (NOF CORPORATION), GS-020 (NOF CORPORATION)) can be recited. "Another lipid component" is used, for example, in 0.25 to 4 mol for 1 mol of the present inventive compound. Use of the present inventive compound mixed with another lipid component (in particular, cholesterol, phosphatidylcholine and a polyethyleneglycol lipid) is preferable. Preferred embodiments in the case where the present inventive compound is used by being mixed with another lipid component is a mixture of 1 to 4 mol of the present inventive compound, 0 to 3 mol of cholesterol, 0 to 2 mol of phosphatidylcholine and 0 to 1 mol of a polyethyleneglycol lipid.

The concentration of the present inventive compound or the concentration of the present inventive compound and another lipid component in an organic solvent solution is preferably 0.5 to 100 mg/mL.

As the organic solvent, for example, methanol, ethanol, 1-propanol, 2-propanol, 1-butanol, tert-butanol, acetone, acetonitrile, N,N-dimethylformamide, dimethylsulfoxide, or a mixture thereof can be recited. The organic solvent may contain 0 to 20% of water or a buffer solution.

As the buffer solution, acidic buffer solutions (e.g. acetate buffer solution, citrate buffer solution) or neutral buffer solutions (e.g. 4-(2-hydroxyethyl)-1-piperazineethanesulfonic acid, (HEPE) buffer solution, tris(hydroxymethyl)aminomethane (Tris) buffer solution, a phosphate buffer solution, phosphate buffered saline (PBS)) can be recited.

In the case where a micro fluid mixing system is used for mixing, preference is given to mixing 1 part of an organic solvent solution with 1 to 5 parts of water or a buffer solution. In addition, in said system, the flow rate of the mixture (a mixture solution of an organic solvent solution and water or a buffer solution) is preferably 0.1 to 10 mL/min, and the temperature preferably is 15 to 45° C.

The present inventive composition can be produced, as a particle suspension comprising the composition, by having added an active ingredient (preferably a nucleic acid) into water or a buffer solution when the lipid particles or a suspension of the lipid particles is produced. Addition of the active ingredient in a manner to render the concentration of the active ingredient in water or a buffer solution 0.05 to 2.0 mg/mL is preferable.

In addition, the present inventive composition can be produced as a particle suspension comprising a composition by admixing lipid particles or a lipid particle suspension with an active ingredient with a method known per se.

The content of the present inventive compound in the present inventive composition preferably is 20 to 80 weight %.

The content of an active ingredient in the present inventive composition preferably is 1 to 20 weight %.

A suspension medium of the lipid particles or that for the components can be substituted with water or a buffer solution by dialysis. For the dialysis, ultrafiltration membrane of molecular weight cutoff 10 to 20K is used to carry out at 4° C. to room temperature. The dialysis may repeatedly be carried out. For the dialysis, tangential flow filtration may be used.

An analytical method for the present inventive lipid particles or composition is explained hereinbelow.

A particle size of the lipid particles or composition can be calculated as a Z-average particle size using Zetasizer Nano ZS (Malvern Instruments) on cumulant analysis of an autocorrelation function. A particle size (mean particle size) of the lipid particles or composition is preferably 10 to 200 nm.

A concentration and encapsulation rate of an active ingredient (in particular, a nucleic acid) in the present inventive composition can be measured Quant-iT™ RiboGreen trademark registered) (Invitrogen). The above mentioned concentration is calculated using the standard curve of an active ingredient (e.g. a nucleic acid (in particular, siRNA, mRNA)), and encapsulation rate can be calculated based on a difference in fluorescent intensity with or without addition of Triton-X100.

The present invention is described in further detail with the following Examples and Test Examples; these do not limit the present invention by any means and, without going beyond the scope of the present invention, changes may be made.

In the Examples below, the term "room temperature" usually means approximately 10° C. to approximately 35° C. A ratio used for a mixed solvent represents a volume ratio unless otherwise specified. Unless otherwise specified, % represents wt %.

The term "NH" in silica gel column chromatography represents that an aminopropylsilane-bound silica gel was used and "Diol" represents that an 3-(2,3-dihydroxypropoxy)propylsilane-bound silica gel was used. A ratio used for elution solvents represents a volume ratio unless otherwise specified.

In the Examples and Test Examples below, the following abbreviations are used:
MS: mass spectrum
M: molar concentration
N: normal
$CDCl_3$: deuterated chloroform
$^1$H NMR: proton nuclear magnetic resonance
MALDI: Matrix-assisted laser desorption/ionization
TOFMS: Time-of-flight mass spectrometry
CHCA: α-cyano-4-hydroxycinnamic acid
DMAP: N,N-dimethyl-4-aminopyridine
THF: tetrahydrofuran
DMF: N,N-dimethylformamide
DPPC: dipalmitoylphosphatidylcholine $^1$H NMR spectra were measured by Fourier transform NMR. ACD/SpecManager (trade name) or the like was used in the analysis. No mention is made of very broad peaks for protons of hydroxyl groups, amino groups and the like.

MS was measured using an MALDI/TOFMS. CHCA was used as a matrix. Data presented are the experimentally measured values (found). In general, molecular ion peaks are observed; in the case of, for example, a compound having a tert-butoxycarbonyl group, a fragment ion peak derived from the elimination of the tert-butoxycarbonyl group or the tert-butyl group may be observed. In the case of a compound having a hydroxyl group, a fragment ion peak derived from the elimination of $H_2O$ may be observed. In the case of a salt, a molecular ion peak, cationic species, anionic species or fragment ion peak of the free form is usually observed.

EXAMPLES

Synthesis Examples of the Compound

Example 1

3-((5-(dimetylamino)pentanoyl)oxy)-2,2-bis(((2-pentylheptanoyl)oxy)methyl)propyl 2-pentylheptanoate A) 2-pentylheptanoic acid A suspension of sodium hydride (0.5 g, containing 40% of mineral oil) in DMF (10 mL) was stirred under ice cooling, dimethyl malonate was added thereto. Ten minutes later, the mixture was elevated to room temperature and 1-iodopentane (1.95 mL) was added. Eighteen hours later, acetic acid (1 mL) was added to the reaction mixture, which was diluted with ethyl acetate, washed twice with water and once with saturated brine, and then dried over anhydrous sodium sulfate; the solvent was distilled off thereafter under reduced pressure. The residue was purified with silica gel column chromatography (ethyl acetate/hexane). A mixture of the obtained compound, 8 N sodium hydroxide aqueous solution (3.75 mL) and ethanol (10 mL) was stirred at 60° C. for 20 hours. The reaction mixture was diluted with 1 N hydrochloric acid and extracted with ethyl acetate. The extract was washed with saturated brine and dried over anhydrous sodium sulfate. The solvent was thereafter distilled off under reduced pressure. The residue was heated at 160° C. for 1.5 hours and, after cooled to room temperature, purified with silica gel column chromatography (ethyl acetate/hexane) to obtain the title compound (786 mg).

1H NMR (300 MHz, $CDCl_3$) δ 0.77-0.97 (6H, m), 1.16-1.38 (12H, m), 1.39-1.53 (2H, m), 1.54-1.72 (2H, m), 2.26-2.42 (1H, m).

B) 2-(((tert-butyldimetylsilyl)oxy)methyl)-2-(hydroxymethyl)propane-1,3-diol

To a mixture of 2,2-bis(hydroxymethyl)propane-1,3-diol (5.45 g), 1H-imidazole (2.72 g) and DMF (190 mL), a solution of tert-butylchlordimetylsilane (3.01 g) in DMF (10 mL) was added at room temperature. After stirring for 24 hours, the reaction mixture was concentrated under reduced pressure. The residue was diluted with ethyl acetate, washed three times with water and once with saturated brine, and then dried over anhydrous sodium sulfate; the solvent was thereafter distilled off under reduced pressure. The residue was purified with silica gel column chromatography (ethyl acetate/hexane) to obtain the title compound (2.25 g).

1H NMR (300 MHz, CDCl$_3$) δ 0.08 (6H, s), 0.90 (9H, s), 2.53 (3H, t, J=5.5 Hz), 3.66 (2H, s), 3.73 (6H, d, J=5.5 Hz).

C) 2-(hydroxymethyl)-2-(((2-pentylheptanoyl)oxy)methyl)propane-1,3-diylbis(2-pentylheptanoate)

To a solution of 2-(((tert-butyldimetylsilyl)oxy)methyl)-2-(hydroxymethyl)propane-1,3-diol (75.0 mg), DMAP (37.0 mg) and 2-pentylheptanoic acid (198 mg) in DMF (0.75 mL), 1-ethyl-3-(3-dimetylaminopropyl) carbodiimide hydrochloride (230 mg) was added at room temperature. After stirring for 18 hours, ethyl acetate was added to the reaction mixture, which was washed twice with water and once with saturated brine, and then dried over anhydrous sodium sulfate; the solvent was distilled off under reduced pressure. The residue was purified with silica gel column chromatography (ethyl acetate/hexane). The obtained compound was dissolved into THF (0.6 mL) and a solution of fluorotetra-n-butylammonium in THF (1 M, 0.66 mL) and acetic acid (0.218 mL) was added thereto at room temperature. After stirring for four days, the reaction mixture was concentrated under reduced pressure. The residue was diluted with ethyl acetate, washed with water and saturated brine, and dried over anhydrous sodium sulfate. The solvent was thereafter distilled off under reduced pressure. The residue was purified with silica gel column chromatography (ethyl acetate/hexane) to obtain the title compound (189 mg).

1H NMR (300 MHz, CDCl$_3$) δ0.79-0.95 (18H, m), 1.14-1.36 (36H, m), 1.38-1.65 (12H, m), 2.29-2.43 (3H, m), 2.69 (1H, t, J=7.2 Hz), 3.47 (2H, d, J=7.2 Hz), 4.11 (6H, s).

D) 3-((5-(dimetylamino)pentanoyl)oxy)-2,2-bis(((2-pentylheptanoyl)oxy)methyl)propyl 2-pentylheptanoate To a mixture of 2-(hydroxymethyl)-2-(((2-pentylheptanoyl)oxy)methyl)propane-1,3-diylbis(2-pentylheptanoate) (189 mg), DMAP (16.9 mg), 5-(dimethylamino)pentanoic acid hydrochloride (60.3 mg) and DMF (0.8 mL), 1-ethyl-3-(3-dimetylaminopropyl) carbodiimide hydrochloride (69.0 mg) was added at room temperature. After stirring for one hour, ethyl acetate was added to the reaction mixture, which was washed once with saturated sodium hydrogencarbonate solution, twice with water and once with saturated brine, and then dried over anhydrous sodium sulfate; the solvent was thereafter distilled off under reduced pressure. The residue was purified with silica gel column chromatography (diol, ethyl acetate/hexane) to obtain the title compound (149 mg).

1H NMR (300 MHz, CDCl$_3$) δ0.80-0.92 (18H, m), 1.15-1.35 (36H, m), 1.37-1.66 (16H, m), 2.20 (6H, s), 2.22-2.42 (7H, m), 4.10 (8H, s).

Example 7

3-((5-(dimetylamino)pentanoyl)oxy)-2,2-bis(((3-pentyloctanoyl)oxy)methyl)propyl 3-pentyloctanoate A) 3-pentyloctanoic acid A suspension of sodium hydride (1.12 g, containing 40% of mineral oil) in THF (40 mL) was stirred under ice cooling, ethyl 2-(diethoxyphosphoryl) acetate (6.01 mL) was added thereto. Ten minutes later, the mixture was elevated to room temperature and undecane-6-one (4.10 mL) was added thereto. After stirring for 24 hours at 50° C., the reaction mixture was concentrated under reduced pressure. The residue was diluted with ethyl acetate, washed with saturated brine, and then dried over anhydrous sodium sulfate; the solvent was thereafter distilled off under reduced pressure. The residue was purified with silica gel column chromatography (ethyl acetate/hexane). A mixture of the obtained compound, 10% palladium-carbon (100 mg) and ethanol (100 mL) was stirred under hydrogen atmosphere for 18 hours. The reaction mixture was filtered and the filtrate was concentrated under reduced pressure. To the residue a solution of 8 N sodium hydroxide (10.6 mL) and ethanol (40 mL) was added, and stirred for one hour at 60° C. The reaction mixture was concentrated under reduced pressure, 6 N hydrochloric acid was added thereto, and extracted with ethyl acetate. The extract was washed with saturated brine and dried over anhydrous sodium sulfate. The solvent was thereafter distilled off under reduced pressure. The residue was purified with silica gel column chromatography (ethyl acetate/hexane) to obtain the title compound (3.47 g).

$^1$H NMR (300 MHz, CDCl$_3$) δ0.81-0.95 (6H, m), 1.15-1.43 (16H, m), 1.74-1.96 (1H, m), 2.28 (2H, d, J=6.8 Hz).

B) 2-(((tert-butyldimetylsilyl)oxy)methyl)-2-(((3-pentyoctanoyl)oxy)methyl)propane-1,3-diyl bis(3-pentyloctanoate)

To a solution of 2-(((tert-butyldimetylsilyl)oxy)methyl)-2-(hydroxymethyl)propane-1,3-diol (751 mg), DMAP (367 mg) and 3-pentyloctanoic acid (2.12 g) in DMF (10 mL), 1-ethyl-3-(3-dimetylaminopropyl)carbodiimide hydrochloride (2.07 g) was added at room temperature. After stirring for one hour, ethyl acetate was added to the reaction mixture, which was washed with saturated sodium hydrogencarbonate solution, twice with water and once with saturated brine, and then dried over anhydrous sodium sulfate; the solvent was thereafter distilled off under reduced pressure. The residue was purified with silica gel column chromatography (NH, ethyl acetate/hexane) to obtain the title compound (2.50 g) was obtained.

1H NMR (300 MHz, CDCl$_3$) δ0.03 (6H, s), 0.76-0.96 (27H, m), 1.11-1.39 (48H, m), 1.75-1.92 (3H, m), 2.23 (6H, d, J=6.8 Hz), 3.58 (2H, s), 4.07 (6H, s).

C) 2-(hydroxymethyl)-2-(((3-pentyloctanoyl)oxy)methyl)propane-1,3-diylbis(3-pentyloctanoate)

2-(((tert-butyldimetylsilyl)oxy)methyl)-2-(((3-pentyloctanoyl)oxy)methyl)propane-1,3-diyl bis(3-pentyloctanoate) (2.50 g) was dissolved into THF (6.0 mL) and a mixture of a solution of fluorotetra-n-butylammonium in THF (1 M, 6.55 mL) and acetic acid (2.17 mL) was added thereto at room temperature. After stirring for four days, the reaction mixture was concentrated under reduced pressure. The residue was diluted with ethyl acetate, washed with water and saturated brine, and then dried over anhydrous sodium sulfate. The solvent was thereafter distilled off under reduced pressure. The residue was purified with silica gel column chromatography (ethyl acetate/hexane) to obtain the title compound (2.05 g).

¹H NMR (300 MHz, CDCl₃) 0.81-0.96 (18H, m), 1.13-1.40 (48H, m), 1.73-1.92 (3H, m), 2.26 (6H, d, J=6.8 Hz), 2.56 (1H, t, J=7.0 Hz), 3.48 (2H, d, J=7.0 Hz), 4.10 (6H, s).

D) 3-((5-(dimethylamino)pentanoyl)oxy)-2,2-bis(((3-pentyloctanoyl)oxy)methyl)propyl 3-pentyloctanoate To a mixture of 2-(hydroxymethyl)-2-(((3-pentyloctanoyl)oxy)methyl)propane-1,3-diyl bis(3-pentyloctanoate) (2.05 g), DMAP (173 mg), 5-(dimethylamino)pentanoic acid hydrochloride (822 mg) and DMF (8.0 mL), 1-ethyl-3-(3-dimethylaminopropyl)carbodiimide hydrochloride (976 mg) was added at room temperature. After stirring for one hour, ethyl acetate was added to the reaction mixture, washed once with saturated sodium hydrogencarbonate solution, twice with water and once with saturated brine, and then dried over anhydrous sodium sulfate; the solvent was thereafter distilled off under reduced pressure. The residue was purified with silica gel column chromatography (ethyl acetate/hexane, ethyl acetate/methanol) to obtain the title compound (2.24 g).

1H NMR (300 MHz, CDCl₃) δ0.81-0.92 (18H, m), 1.15-1.37 (48H, m), 1.42-1.53 (2H, m), 1.59-1.69 (2H, m), 1.73-1.90 (3H, m), 2.18-2.38 (16H, m), 4.10 (8H, s).

Example 8

N,N,N-trimethyl-5-oxo-5-(3-((3-pentyloctanoyl)oxy)-2,2-bis(((3-pentyloctanoyl)oxy)methyl)propoxy)pentane-1-aminium iodide To a solution of 3-((5-(dimethylamino)pentanoyl)oxy)-2,2-bis(((3-pentyloctanoyl)oxy)methyl)propyl 3-pentyloctanoate (50.0 mg) in ethyl acetate (0.6 mL), methyl iodide (7.34 μL) was added at room temperature. After stirring for two hours, the reaction mixture was concentrated under reduced pressure. The residue was purified with silica gel column chromatography (NH, ethyl acetate/hexane) to obtain the title compound (46.8 mg).

¹H NMR (300 MHz, CDCl₃) δ0.79-0.97 (18H, m), 1.13-1.40 (48H, m), 1.68-1.92 (7H, m), 2.25 (6H, d, J=7.2 Hz), 2.46 (2H, t, J=6.4 Hz), 3.46 (9H, s), 3.61-3.75 (2H, m), 4.10 (8H, s).

In accordance with a method given in each Example or a method similar thereto, compounds of Examples 2 to 6 and Examples 9 to 10 were produced listed in the following tables. As regards these Examples, with Examples 1, 7 and 8, a name of the compound, chemical structure and a mass number actually measured when produced (in the table, denoted by MS) are given in Table 1. In the column of "Salt", a cation constituting the compound is given.

TABLE 1-1

| Ex. No. | IUPAC Name | Structure | Salt | MS |
|---|---|---|---|---|
| 1 | 3-((5-(dimethylamino)pentanoyl)oxy)-2,2-bis(((2-pentylheptanoyl)oxy)methyl)propyl 2-pentyl heptanoate | 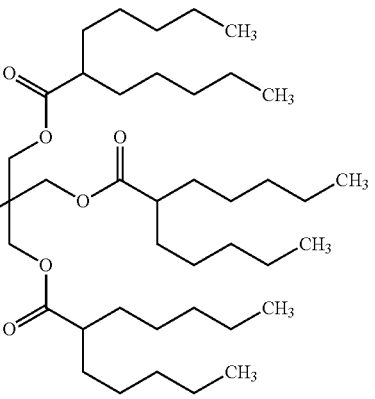 | | 810.670 |
| 2 | 3-((4-(dimethylamino)butanoyl)oxy)-2,2-bis(((2-pentylheptanoyl)oxy)methyl)propyl 2-pentyl heptanoate | 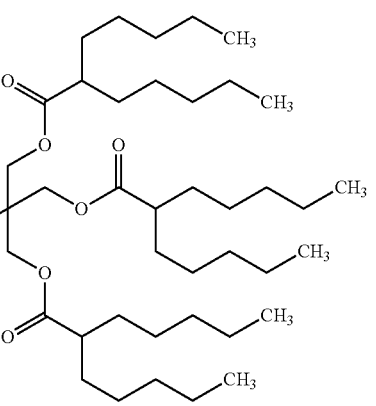 | | 796.530 |

TABLE 1-1-continued
| Ex. No. | IUPAC Name | Structure | Salt | MS |
|---|---|---|---|---|
| 3 | 3-(2-(butylhexanoyl)oxy)-2-(((2-butylhexanoyl)oxy)methyl)-2-(((5-(dimethylamino)pentanoyl)oxy)methyl)propyl 2-butyl hexanoate | 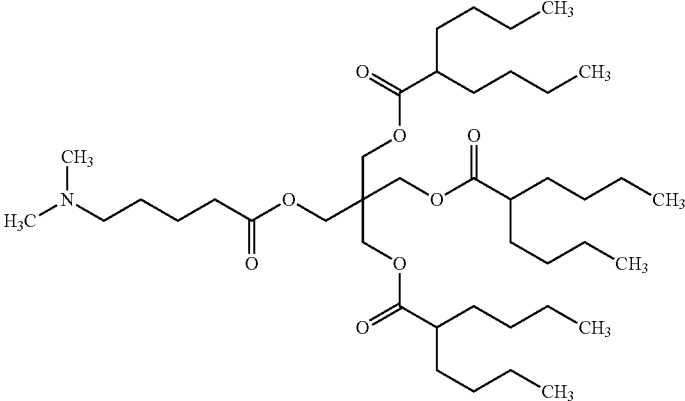 [SMILES: CCCCC(CCCC)C(=O)OCC(COC(=O)CCCCN(C)C)(COC(=O)C(CCCC)CCCC)COC(=O)C(CCCC)CCCC] | | 726.696 |
| 4 | 3-((2-butylhexanoyl)oxy)-2-(((2-butylhexanoyl)oxy)methyl)-2-((4-(dimethylamino)butanoyloxy)methyl)propyl 2-butyl hexanoate | 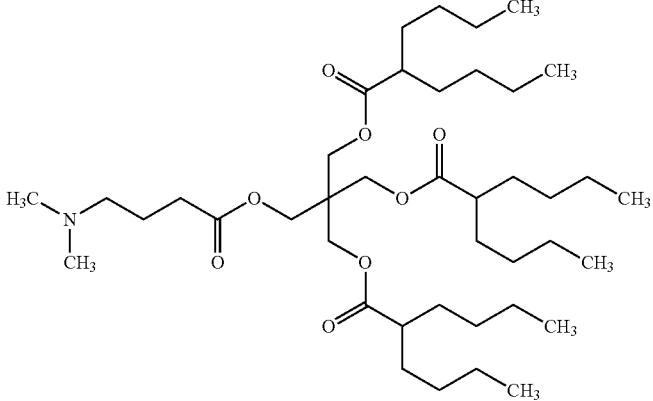 [SMILES: CCCCC(CCCC)C(=O)OCC(COC(=O)CCCN(C)C)(COC(=O)C(CCCC)CCCC)COC(=O)C(CCCC)CCCC] | | 712.628 |
| 5 | 3-((5-(dimethylamino)pentanoyl)oxy)-2,2-bis(((2-hexyloctanoyl)oxy)methyl)propyl 2-hexyl octanoate | 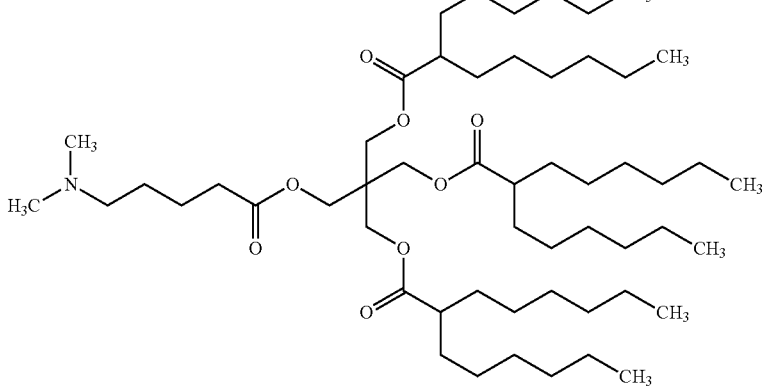 | | 894.818 |

TABLE 1-1-continued

| Ex. No. | IUPAC Name | Structure | Salt | MS |
|---|---|---|---|---|
| 6 | 3-((4-(dimethylamino)butanoyl)oxy)-2,2-bis(((2-hexyloctanoyl)oxy)methyl)propyl 2-hexyl octanoate | 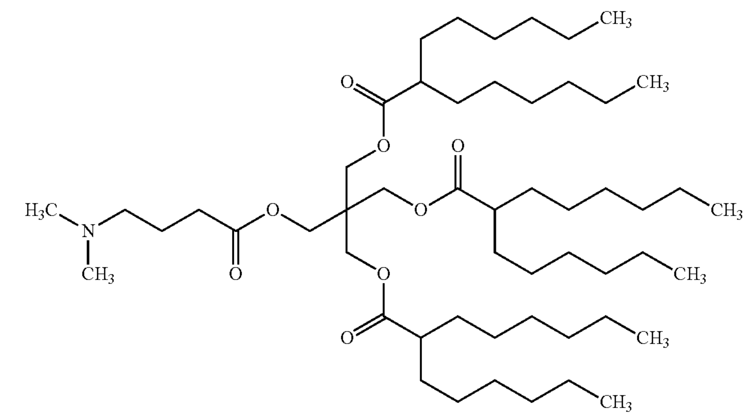 [SMILES: CCCCCCC(CCCCCC)C(=O)OCC(COC(=O)CCCN(C)C)(COC(=O)C(CCCCCC)CCCCCC)COC(=O)C(CCCCCC)CCCCCC] | | 880.740 |
| 7 | 3-((5-(dimethylamino)pentanoyl)oxy)-2,2-bis(((3-pentyloctanoyl)oxy)methyl)propyl 3-pentyl octanoate | 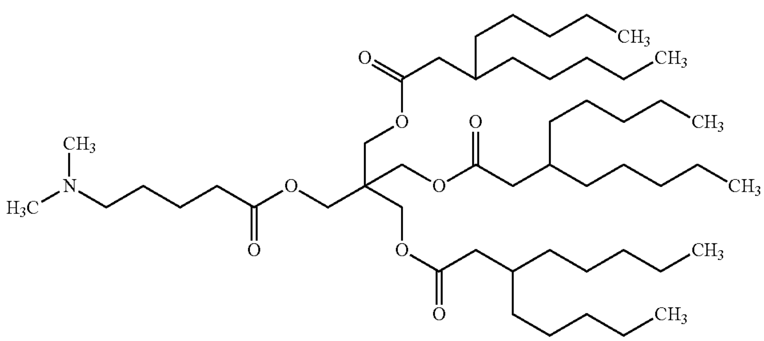 [SMILES: CCCCCC(CCCCC)CC(=O)OCC(COC(=O)CCCCN(C)C)(COC(=O)CC(CCCCC)CCCCC)COC(=O)CC(CCCCC)CCCCC] | | 852.707 |
| 8 | N,N,N-trimethyl-5-oxo-5-(3-((3-pentyloctanoyl)oxy)-2,2-bis(((3-pentyloctanoyl)oxy)methyl)propoxy)pentan-1-aminium iodide | 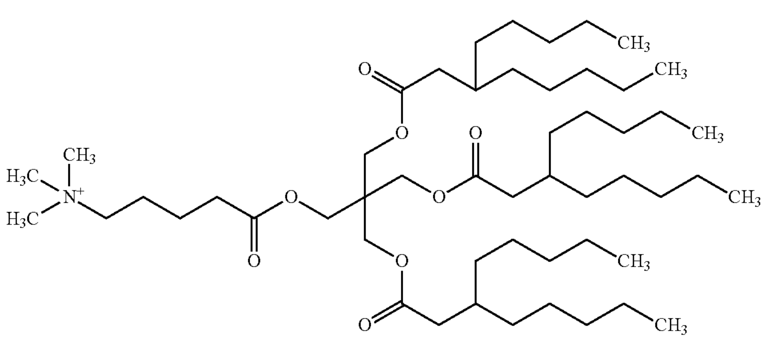 [SMILES: CCCCCC(CCCCC)CC(=O)OCC(COC(=O)CCCC[N+](C)(C)C)(COC(=O)CC(CCCCC)CCCCC)COC(=O)CC(CCCCC)CCCCC] | I− | 866.609 |
| 9 | 3-((4-(dimethylamino)butanoyl)oxy)-2,2-bis(((3-pentyloctanoyl)oxy)methyl)propyl 3-pentyl octanoate | 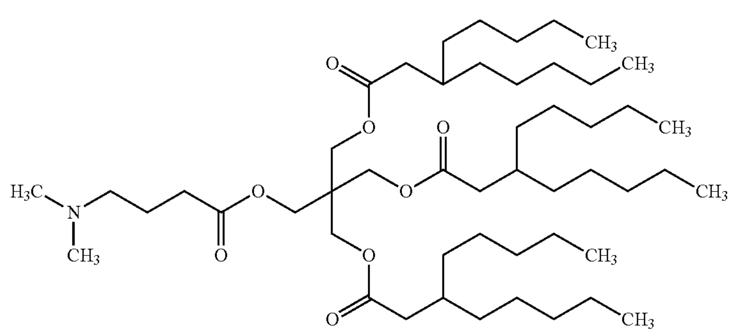 [SMILES: CCCCCC(CCCCC)CC(=O)OCC(COC(=O)CCCN(C)C)(COC(=O)CC(CCCCC)CCCCC)COC(=O)CC(CCCCC)CCCCC] | | 838.752 |

TABLE 1-1-continued

| Ex. No. | IUPAC Name | Structure | Salt | MS |
|---|---|---|---|---|
| 10 | 3-((N,N-dimethyl-beta-alanyl)oxy)-2,2-bis(((3-pentyloctanoyl)oxy)methyl)propyl 3-pentyl octanoate | 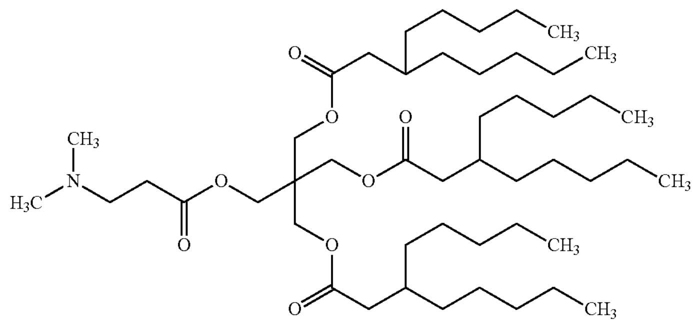 [SMILES: CCCCCC(CCCCC)CC(=O)OCC(COC(=O)CCN(C)C)(COC(=O)CC(CCCCC)CCCCC)COC(=O)CC(CCCCC)CCCCC] | | 824.796 |

Production Examples of the Present Inventive Composition

Example 11

The lipid mixture (the compound obtained in Example 7:DPPC:Cholesterol:GS-020=60:10.6:28:1.4, mol ratio) was dissolved into 90% EtOH and 10% 25 mM acetate buffer solution of pH 4.0 to obtain a lipid solution in 7.4 mg/ml. Luciferase (luc) siRNA and Factor VII (FVII) siRNA (see Table 2) was added at an equivalent amount and dissolved into 25 mM acetate buffer solution of pH4.0 to obtain 0.15 mg/ml of a nucleic acid solution. The obtained lipid solution and nucleic acid solution were mixed at room temperature with Asia microfluidic system (Syrris) at a flow rate of 1 ml/min:5 ml/min to obtain a particle suspension comprising the composition above. The obtained suspension was dialyzed using Slide-A-Lyzer (molecular weight cutoff 20K, Thermo scientific) against water at room temperature for 1 hour and against PBS at room temperature for 18 hours. Filtration was then conducted using 0.2 μm syringe filter (Iwaki) and stored at 4° C. The result of analysis is shown in Table 3.

TABLE 2

| Target Gene | Sequence 5'-3' |
|---|---|
| FVII | GGAU(F)C(F)AU(F)C(F)U(F)C(F)AAGU(F)C(F)U(F)U(F)AC(F)tst (SEQ ID NO: 1) GU(F)AAGAC(F)U(F)U(F)GAGAU(F)GAU(F)C(F)C(F)tst (SEQ ID NO: 2) |
| luc | C(M)U(M)U(M)AC(M)GC(M)U(M)GAGU(M)AC(M)U(M)U(M)C(M)GAtst (SEQ ID NO: 3) UCGAAGUACUCAGCGUAAGtst (SEQ ID NO: 4) |

N(M): 2'-OMe RNA,
N(F): 2'-deoxy-2'-fluoro RNA,
t: 2'-deoxythymidine,
s: Phosphorothioate bond

TABLE 3

| Particle size | siRNAconcentration (μg/μL) | Encapsulation rate |
|---|---|---|
| 78 nm | 0.098 | 96% |

Example 12

The lipid mixture (the compound obtained in Example 7:DPPC:Cholesterol:GS-020=60:10.6:28:1.4, mol ratio) was dissolved into 90% EtOH and 10% 25 mM acetate buffer solution of pH 4.0 to obtain a lipid solution in 8.9 mg/ml. Hypoxanthine-guanine phosphoribosyltransferase (HPRT) siRNA (see Table 4) was dissolved into 25 mM acetate buffer solution of pH4.0 to obtain 0.25 mg/ml of a nucleic acid solution. The obtained lipid solution and nucleic acid solution were mixed at room temperature with Asia microfluidic system at a flow rate of 1 ml/min:3 ml/min to obtain a suspension comprising the composition. The obtained solution was dialyzed using Slide-A-Lyzer (molecular weight cutoff 20K) against water at room temperature for one hour and against PBS at room temperature for 18 hours. In addition, under heightened pressure with filled nitrogen gas, the solution was dialyzed against PBS at 4° C. to concentrate the solution. Filtration was then conducted using 0.2 μm or 0.45 μm syringe filter and stored at 4° C. The result of analysis is shown in Table 5.

TABLE 4

| Target Gene | Sequence 5'-3' |
|---|---|
| HPRT | U(M)C(M)C(M)U(M)AU(M)GAC(M)U(M)GU(M)AGAU(M)U(M)U(M)U(M)tst (SEQ ID NO: 5) AAAAUCU(M)AC(M)AGUC(M)AU(M)AGGAtst (SEQ ID NO: 6) |

N(M): 2'-OMe RNA,
N(F): 2'-deoxy-2'-fluoro RNA,
t: 2'-deoxythymidine,
s: Phosphorothioate bond

TABLE 5

| Particle size | siRNAconcentration (μg/μL) | Encapsulation rate |
|---|---|---|
| 81 nm | 1.36 | 98% |

Example 13

The lipid mixture (the compound obtained in Example 7:the compound obtained in Example 8:DPPC:Cholesterol:GM-020=59.1:0.9:10.6:28:1.4, mol ratio) was dissolved into 90% EtOH and 10% 25 mM acetate buffer solution of pH 4.0 to obtain a lipid solution in 7.6 mg/ml. HPRT siRNA (see Table 4) was dissolved into 25 mM acetate buffer solution of pH4.0 to obtain 0.21 mg/ml of a nucleic acid solution. The obtained lipid solution and nucleic acid solution were mixed at room temperature with Asia microfluidic system at a flow rate of 1 ml/min:3 ml/min to obtain a dispersion comprising the composition. The obtained solution was dialyzed using Slide-A-Lyzer (molecular weight cutoff 20K) against water at room temperature for one hour and against PBS at room temperature for 18 hours. Filtration was then conducted using 0.2 μm syringe filter and stored at 4° C. The result of analysis is shown in Table 6.

TABLE 6

| Particle size | siRNA concentration (μg/μL) | Encapsulation rate |
|---|---|---|
| 80 nm | 0.286 | 98% |

Example 14

The lipid mixture (the compound obtained in Example 1:DPPC:Cholesterol:GM-020=60:10.6:28:1.4, mol ratio) was dissolved into 90% EtOH and 10% RNase free water to obtain a lipid solution in 8.4 mg/ml. Fluc mRNA (TriLink BioTechnologies) was dissolved into 10 mM citrate buffer solution of pH3.0 to obtain 0.125 mg/ml of a nucleic acid solution. The obtained lipid solution and nucleic acid solution were mixed at room temperature with Asia microfluidic system at a flow rate of 1 ml/min:3 ml/min to obtain a suspension comprising the composition. The obtained solution was dialyzed using Slide-A-Lyzer (molecular weight cutoff 20K) against water at 4° C. for one hour and against PBS at 4° C. for 18 hours. Filtration was then conducted using 0.2 μm syringe filter and stored at 4° C. The result of analysis is shown in Table 7.

TABLE 7

| Particle size | mRNA concentration (μg/μL) | Encapsulation rate |
|---|---|---|
| 78 nm | 0.065 | 98% |

Example 15

The lipid mixture (the compound obtained in Example 7:DPPC:Cholesterol:GM-020=60:10.6:28:1.4, mol ratio) was dissolved into 90% EtOH and 10% RNase free water to obtain a lipid solution in 8.7 mg/ml. Fluc mRNA (TriLink BioTechnologies) was dissolved into 10 mM citrate acid buffer solution of pH3.0 to obtain 0.125 mg/ml of a nucleic acid solution. The obtained lipid solution and nucleic acid solution were mixed at room temperature with Asia microfluidic system at a flow rate of 1 ml/min:3 ml/min to obtain a suspension comprising the composition. The obtained solution was dialyzed using Slide-A-Lyzer (molecular weight cutoff 20K) against water at 4° C. for one hour and against PBS at 4° C. for 18 hours. Filtration was then conducted using 0.2 μm syringe filter and stored at 4° C. The result of analysis is shown in Table 8.

TABLE 8

| Particle size | mRNA concentration (μg/μL) | Encapsulation rate |
|---|---|---|
| 85 nm | 0.125 | 97% |

TEST EXAMPLES

Test Example 1

In Vivo Knockdown Test in the Liver

FVII is an important coagulation factor in the extrinsic blood coagulation reaction, being produced in hepatocytes and secreted into the blood; plasma FVII concentration can be measured by simple colorimetric analysis using a plate, so FVII is a typical model useful for measuring knockdown (KD) in liver parenchymal cells by siRNA. Phosphate buffered saline (PBS) or the dispersion (0.25 mg/kg as FVII siRNA) dialyzed in Example 11 was administered to BALB/cA mouse (9 weeks old, female, Japan Clea Corporation) in tail vein, and blood was collected 24 hours after administration (N=3). The blood was immediately mixed with EDTA (final concentration 0.1%) and centrifuged at 5000 g for 10 minutes. The FVII concentration of the supernatant was measured using BIOPHEN FACTOR 7 CHROMOGENIC ASSAY (HYPHEN BioMed). The residual ratio was calculated based on the FVII concentration in the PBS administration group being regarded as 100%. As shown in Table 9, the FVII concentration in the Example 11 administration group was 6.9%. This result clearly indicates that siRNA can be introduced into the liver by using the present inventive compound.

TABLE 9

| | Residual ratio at 0.25 mg/kg (%) |
|---|---|
| Example 11 | 6.9 |

Test Example 2

In Vivo Knockdown Test on Cancer Cells

HCT 116 cells (human colon cancer cell line, American Type Culture Collection (ATCC), 1×10$^6$ cells/mouse) and Matrigel (Becton Dickinson and Company, 356237, 50% in liquid volume) were subcutaneously transplanted in the right flank of nude mice (BALB/c-nu/nu, 6 weeks old, female, Charles River Japan). Those mice were grouped based on the tumor volume after 15 days (four animals per group; mean tumor volume was 521 to 544 mm$^3$). PBS or the particle suspension (10 mg/kg as HPRT siRNA) dialyzed in Example 12 was administered from the tail vein and 48 hours after the administration the mice were euthanized by cervical dislocation under 2.5% isoflurane anesthesia, and the subcutaneous tumor was excised and quickly frozen on dry ice after weighing. The frozen mass of the subcutaneous tumor was homogenized by adding TRIzol Reagent (Invitrogen), and then chloroform was added and centrifuged to separate the aqueous phase containing RNA. The aqueous phase was extracted and purified using RNeasy mini Kit (QIAGEN) to obtain the total RNA. SuperScript VILO cDNA Synthesis Kit (Invitrogen) was used to conduct reverse transcription and the mRNA amount of human HPRT (hHPRT) was measured by qPCR method. Probes and primers for hHPRT were obtained from Applied Biosystems Inc. (ABI) (Probe: FAM-TAMRA, 5'-CCATCACATTG-TAGCCCTCTGTGTGCTC-3' (SEQ ID NO: 7); Forward primer: 5'-CGTCTTGCTCGAGATGTGATG-3' (SEQ ID NO: 8); Reverse primer: 5'-CCAGCAGGTCAG-CAAAGAATT-3' (SEQ ID NO: 9)). As the internal standard gene human actin beta (hACTB) was used and the amount of mRNA of hHPRT was calculated based on the value of PBS administered group being regarded as 100%. The probe and primer of hACTB were obtained from ABI (Probe: FAM-TAMRA, 5'-ATCAAGATCATTGCTCCTCCT-GAGCGC-3' (SEQ ID NO: 10); Forward primer: 5'-CCTG-GCACCCAGCACAAT-3' (SEQ ID NO: 11); Reverse primer: 5'-GCCGATCCACACGGAGTACT-3' (SEQ ID NO: 12)). The result was, as shown in Table 9, the residual amount of hHPRT in the group administered with the particle suspension after dialysis conducted in Example 12 relative to the PBS administration group was 48%. This result clearly indicates that siRNA can be introduced into tumor cells by using the present inventive compound.

TABLE 10

| | Residual ratio at 10 mg/kg (%) |
|---|---|
| Example 12 | 48 |

Test Example 3

In Vivo Knockdown Test on Adipose Tissues

HT29-Luc cells (a human colon cancer cell line HT29 (purchased from ATCC) stably expressing luciferase gene, $5 \times 10^6$ cells/mouse) and Matrigel (Becton Dickinson and Company, 356237, 50% in liquid volume) were subcutaneously transplanted in the right flank of nude mice (BALB/c-nu/nu, 7 weeks old, female, Charles River Japan). Those mice were grouped based on the tumor volume after 16 days (four animals per group; mean tumor volume was 271 to 288 mm$^3$). PBS or the particle suspension (5 mg/kg as HPRT siRNA) obtained in a similar manner as conducted in Example 12 was administered from the tail vein and 48 hours after the administration the mice were euthanized by cervical dislocation under 2.5% isoflurane anesthesia, and then the periportal fat was excised and quickly frozen on dry ice after weighing. The frozen adipose tissue was homogenized by adding TRIzol Reagent (Invitrogen), chloroform was added, and then centrifuged to separate the aqueous phase containing RNA. The aqueous phase was extracted and total RNA was purified using RNeasy mini Kit (QIAGEN). SuperScript VILO cDNA Synthesis Kit (Invitrogen) was used to conduct reverse transcription and the mRNA amount of mouse HPRT (mHPRT) was measured by qPCR method. Probes and primers for mHPRT were obtained from ABI (Mm01545399_m1). As the internal standard gene mouse actin beta (mACTB) was used and the amount of mRNA of mHPRT was calculated based on the value of PBS administered group being regarded as 100%. The probe and primer of mACTB were purchased from ABI (4352341E). As a result, the relative residual amount of mHPRT in the group administered with the particle suspension obtained in a similar manner as conducted in Example 12 was 44% (Table 11). This result clearly indicates that siRNA can be introduced into adipose tissues by using the present inventive compound.

TABLE 11

| | Residual ratio at 5 mg/kg (%) |
|---|---|
| Example 12 | 44 |

Test Example 4

In Vivo Knockdown Test on the Bone Marrow

HT29-Luc cells (a human colon cancer cell line HT29 (purchased from ATCC) stably expressing luciferase gene, $5 \times 10^6$ cells/mouse) and Matrigel (Becton Dickinson and Company, 356237, 50% in liquid volume) were subcutaneously transplanted in the right flank of nude mice (BALB/c-nu/nu, 6 weeks old, female, Japan Clea Corporation). Those mice were grouped based on the tumor volume after 17 days (four animals per group; mean tumor volume was 321 to 329 mm$^3$). PBS or the particle suspension (5 mg/kg as HPRT siRNA) obtained in a similar manner as conducted in Example 12 was administered from the tail vein and 48 hours after the administration the mice were euthanized by cervical dislocation under 2.5% isoflurane anesthesia. The bone marrow cells were collected from the femurs and extracted and total RNA was purified using RNeasy mini Kit (QIAGEN). SuperScript VILO cDNA Synthesis Kit (Invitrogen) was used to conduct reverse transcription and the mRNA amount of mouse HPRT (mHPRT) was measured by qPCR method. Probes and primers for mHPRT were obtained from ABI (Mm01545399_m1). As the internal standard gene mouse actin beta (mACTB) was used and the amount of mRNA of mHPRT was calculated based on the value of PBS administered group being regarded as 100%. The probe and primer of mACTB were purchased from ABI (4352341E). As a result, the relative residual amount of mHPRT in the group administered with the particle suspension obtained in a similar manner as conducted in Example 12 was 56% (Table 12). This result clearly indicates that siRNA can be introduced into the bone marrow by using the present inventive compound.

TABLE 12

| | Residual ratio at 5 mg/kg (%) |
|---|---|
| Example 12 | 56 |

Test Example 5

In Vitro Knockdown Test on Suspended Hematopoietic Cells Ramos

Ramos cells (human B-cell lymphoma derived cell line) were seeded in a 96-well plate at a density of 1×104 cells/well (RPMI1640 basic, 10% FBS, penicillin-streptomycin). A mixture of PBS, HPRT siRNA and Lipofectamine (Trademark registered) as well as RNAiMAX (Life technologies)(mixed in accordance with a protocol) or a particle suspension after being dialyzed in Example 13 was added (N=3, the final concentration of HPRT siRNA was 100 nM) and the cells were collected after 48 hours. The cells were extracted and total RNA was purified with RNeasy mini Kit (QIAGEN). SuperScript VILO cDNA Synthesis Kit was used to conduct reverse transcription and the mRNA amount of hHPRT) was measured by qPCR method. Probes and primers for hHPRT were the same as those used in Test Example 2. As the internal standard gene hACTB was used and the amount of mRNA of hHPRT was calculated based on the value of PBS administered group being regarded as 100%. The probe and primer of hACTB were the same as those used in Test Example 2. As a result, the relative residual amount of hHPRT in the group treated with the particle suspension obtained in a similar manner as conducted in Example 12 was 17%. On the other hand, that in the group treated with RNAiMAX was 109% (Table 13). This result clearly indicates that siRNA can be introduced into the hematopoietic cells by using the present inventive compound.

TABLE 13

| | Residual ratio at 100 nM (%) |
|---|---|
| RNAiMAX | 109 |
| Example 13 | 17 |

Test Example 6

In Vivo Expression Test of Luciferase

As the animals female BALB/c mice were used. The animals, provided at six-week old, were acclimatized under the normal breeding for about three weeks, and the particle suspension dialyzed in Example 14 or 15 (0.25 mg/kg as Fluc mRNA) was administered from the tail vein (N=2). Six hours later, under anesthesia with Isoflurane, 200 μl D-luciferin (15 mg/ml) was intraperitoneally administered; ten minutes after the D-luciferin administration, luminescence in the whole body was observed to calculate an average amount of luminescence using in vivo imaging system (IVIS, Caliper). The test result is shown in Table 14. This result shows that mRNAs can be introduced in vivo by using the present inventive compound.

TABLE 14

| | Amount of luminescence ($10^8$ p/s) |
|---|---|
| Example 14 | 190 |
| Example 15 | 69 |

INDUSTRIAL APPLICABILITY

The present inventive compound, lipid particles or composition makes it possible to efficiently introduce nucleic acids into various cells, tissues or organs. The present inventive compound, lipid particles or composition, therefore, are useful as DDS technology for nucleic acid medicines. In addition, the present inventive compound, lipid particles or composition are available also as a nucleic acid introducing agent for research uses.

The present application is based on a Japanese Patent Application No. 2014-161718 filed in Japan and the content thereof is incorporated into the present description in their entirety.

[Sequence Listing]

The invention claimed is:

1. A compound represented by the formula:

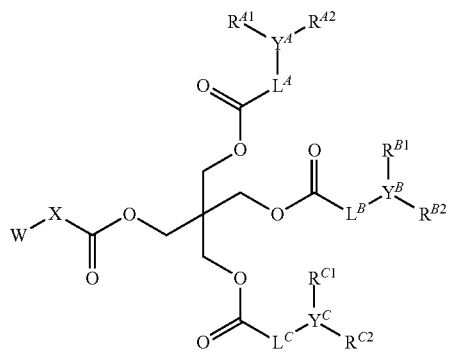

W denotes formula $-NR^1R^2$ or formula $-N^+R^3R^4R^5(Z^{31-})$;

$R^1$ and $R^2$ denote, each independently, a $C_{1-4}$ alkyl group or hydrogen atom;

$R^3$, $R^4$ and $R^5$ denote, each independently, a $C_{1-4}$ alkyl group;

$Z^-$ denotes a negative ion;

X denotes a $C_{1-6}$ alkylene group which may be substituted;

$Y^A$, $Y^B$ and $Y^C$ denote, each independently, a methine group which may be substituted;

$L^A$, $L^B$ and $L^C$ denote, each independently, a methylene group which may be substituted or a bond; and $R^{A1}$, $R^{A2}$, $R^{B1}$, $R^{B2}$, $R^{C1}$ and $R^{C2}$ denote, each independently, a $C_{4-10}$ alkyl group which may be substituted, or a salt thereof.

2. The compound according to claim 1 or a salt thereof, wherein $R^1$, $R^2$, $R^3$, $R^4$ and $R^5$ are a methyl group;

$Z^{31-}$ is a halide ion;

X is an ethylene group, trimethylene group or tetramethylene group;

$Y^A$, $Y^B$ and $Y^C$ are a methine group;

$L^A$, $L^B$ and $L^C$ are, each independently, a bond or methylene group; and $R^{A1}$, $R^{A2}$, $R^{B1}$, $R^{B2}$, $R^{C1}$ and $R^{C2}$ are, each independently, a butyl group, pentyl group or hexyl group.

3. A compound selected from the group consisting of:

3-((5-(dimethylamino)pentanoyl)oxy)-2,2-bis(((2-pentylheptanoyl) oxy)methyl)propyl 2-pentylheptanoate or a salt thereof and 3-((5-(dimethylamino)pentanoyl)oxy)-2,2-bis(((3-pentyloctanoyl) oxy)methyl)propyl 3-pentyloctanoate or a salt thereof.

4. A salt of N,N,N-trimethyl-5-oxo-5-(3-((3-pentyloctanoyl)oxy)-2,2-bis(((3-pentyloctanoyl)oxy)methyl)propoxy)pentane-1-aminium and a negative ion.

5. A lipid particle containing the compound according to claim 1 or a salt thereof.

6. A composition containing an active ingredient and the compound according to claim 1 or a salt thereof.

7. The composition according to claim 6, wherein the active ingredient is a nucleic acid.

8. The composition according to claim 7, wherein the nucleic acid is siRNA or mRNA.

* * * * *